United States Patent [19]
Tan

[11] Patent Number: 5,888,506
[45] Date of Patent: Mar. 30, 1999

[54] METHIONINASE FORMULATIONS

[75] Inventor: Yuying Tan, San Diego, Calif.

[73] Assignee: AntiCancer, Inc., San Diego, Calif.

[21] Appl. No.: 914,377

[22] Filed: Aug. 19, 1997

Related U.S. Application Data

[60] Division of Ser. No. 642,541, May 3, 1996, which is a continuation-in-part of Ser. No. 486,519, Jun. 7, 1995, Pat. No. 5,715,835, and Ser. No. 424,300, filed as PCT/US93/11311 Nov. 13, 1993, Pat. No. 5,690,929, which is a continuation-in-part of Ser. No. 979,165, Nov. 19, 1992, abandoned.

[51] Int. Cl.$^6$ .............................. A61K 38/51; C12N 9/96; C12N 9/88
[52] U.S. Cl. ...................... 424/94.5; 424/94.2; 435/188; 435/232
[58] Field of Search ................................. 424/94.5, 94.2; 435/232, 188

[56] References Cited

PUBLICATIONS

Berezov, T.T. et al. "An improved procedure for isolation and purification of methionine gamma–lyase from Pseudomonase putida." Voprosy Meditsinskoi Khimii (1983), vol. 29, No. 4, pp. 131–135, 1983.

*Primary Examiner*—Kawai Lau
*Attorney, Agent, or Firm*—Morrison & Foerster LLP

[57] ABSTRACT

Improved formulations of methioninase which contain methioninase in crystalline, lyophilized, or conjugated form are disclosed. The methioninase in these compositions has a specific activity of at least 20 U/mg and the formulations are detergent free and contain less than 1 ng endotoxin per mg protein.

19 Claims, 23 Drawing Sheets

FIG. IA

Sequence Range: 1 to 1369

```
            10         20         30         40         50         60
            *          *          *          *          *          *
         GCGGTCTGT  GGAATAAGCT  TATAACAAAC  CACAAGAGGC  GGTTGCCATG  CACGGCTCCA
         CGGCCAGACA  CCTTATTCGA  ATATTGTTTG  GTGTTCTCCG  CCAACGGTAC  GTGCCGAGGT
                                                                Met HisGlySer 70         80         90        100        110        120
            *          *          *          *          *          *
         ACAAGCTCCC  AGGATTTGCC  ACCCGCGCCA  TTCACCATGG  CTACGACCCC  CAGGACCACG
         TGTTCGAGGG  TCCTAAACGG  TGGGCGCGGT  AAGTGGTACC  GATGCTGGGG  GTCCTGGTGC
         AsnLysLeuPro GlyPheAla ThrArgAla IleHisHisGly TyrAspPro GlnAspHis 130        140        150        160        170        180
            *          *          *          *          *          *
         GCGGCGCACT  GGTGCCACCG  GTCTACCAGA  CCGGCGACGTT  CACCTTCCCC  ACCGTGGAAT
         CGCCGCGTGA  CCACGGTGGC  CAGATGGTCT  GGCCGCTGCAA  GTGGAAGGGG  TGGCACCTTA
         GlyGlyAlaLeu ValProPro ValTyrGln ThrAlaThrPhe ThrPhePro ThrValGlu 190        200        210        220        230        240
            *          *          *          *          *          *
         ACGGCGCTGC  GTGCTTTGCC  GGCGAGCAGG  CCGGCCATTT  CTACAGCCGC  ATCTCCAACC
         TGCCGCGACG  CACGAAACGG  CCGCTCGTCC  GGCCGGTAAA  GATGTCGGCG  TAGAGGTTGG
         TyrGlyAlaAla CysPheAla GlyGluGln AlaGlyHisPhe TyrSerArg IleSerAsn
```

FIG. 1B

```
         250        260        270        280        290        300
          *          *          *          *          *          *
CCACCCTCAA CCTGCTGGAA GCACGCATGG CCTCGCTGGA AGGCGGCGAG GCCGGGCTGG
GGTGGGAGTT GGACGACCTT CGTGCGTACC GGAGCGACCT TCCGCCGCTC CGGCCCGACC
ProThrLeuAsn LeuLeuGlu AlaArgMet AlaSerLeuGlu GlyGlyGlu AlaGlyLeu 310        320        330        340        350        360
          *          *          *          *          *          *
CGCTGGCCTC GGGCATGGGG GCGATCACGT CCACGCTATG GACACTGCTG CGCCCCGGTG
GCGACCGGAG CCCGTACCCC CGCTAGTGCA GGTGCGATAC CTGTGACGAC GCGGGGCCAC
AlaLeuAlaSer GlyMetGly AlaIleThr SerThrLeuTrp ThrLeuLeu ArgProGly 370        380        390        400        410        420
          *          *          *          *          *          *
ACGAGGTGCT GCTGGGCAAC ACCCTGTACG GCTGCACCTT TGCCTTCCTG CACCACGGCA
TGCTCCACGA CGACCCGTTG TGGGACATGC CGACGTGGAA ACGGAAGGAC GTGGTGCCGT
AspGluValLeu LeuGlyAsn ThrLeuTyr GlyCysThrPhe AlaPheLeu HisHisGly 430        440        450        460        470        480
          *          *          *          *          *          *
TCGGCGAGTT CGGGGTCAAG CTGCGCCATG TGGACATGGC CGACCTGCAG GCACTGGAGG
AGCCGCTCAA GCCCCAGTTC GACGCGGTAC ACCTGTACCG GCTGGACGTC CGTGACCTCC
IleGlyGluPhe GlyValLys LeuArgHis ValAspMetAla AspLeuGln AlaLeuGlu 490        500        510        520        530        540
          *          *          *          *          *          *
CGGCCATGAC GCCGGCCACC CGGGTGATCT ATTTCGAGTC GCCGGCCAAC CCCAACATGC
GCCGGTACTG CGGCCGGTGG GCCCACTAGA TAAAGCTCAG CGGCCGGTTG GGGTTGTACG
```

FIG. 1C

```
                                    AlaAlaMetThr ProAlaThr TrpValIle TyrPheGluSer ProAlaAsn ProAsnMet
         550        560        570        580        590        600
          *          *          *          *          *          *
    ACATGGCCGA TATCGCCGGC GTGGCGAAGA TTGCAGCCAA GCACGGCGCG ACCGTGGTGG
    TGTACCGGCT ATAGCGGCCG CACCGCTTCT AACGTGCGTT CGTGCCGCGC TGGCACCACC
    HisMetAlaAsp IleAlaGly ValAlaLys IleAlaArgLys HisGlyAla ThrValVal 610        620        630        640        650        660
          *          *          *          *          *          *
    TCGACAACAC CTACTGCACG CCGTACCTGC AACGGCCACT GGAGCTGGGC GCCGACCTGG
    AGCTGTTGTG GATGACGTGC GGCATGGACG TTGCCGGTGA CCTCGACCCG CGGCTGGACC
    ValAspAsnThr TyrCysThr ProTyrLeu GlnTrpProLeu GluLeuGly AlaAspLeu 670        680        690        700        710        720
          *          *          *          *          *          *
    TGGTGCATTC GGCCACCAAG TACCTGAGCG GCCATGGCGA CATCACTGCT GGCATTGTGG
    ACCACGTAAG CCGGTGGTTC ATGGACTCGC CGGTACCGCT GTAGTGACGA CCGTAACACC
    ValValHisSer AlaThrLys TyrLeuSer GlyHisGlyAsp IleThrAla GlyIleVal 730        740        750        760        770        780
          *          *          *          *          *          *
    TGGGCAGCCA GGCACTGGTG GACCGTATAC GTCTGCAGGG CCTCAAGGAC ATGACCGGTG
    ACCCGTCGGT CCGTGACCAC CTGGCATATG CAGACGTCCC GGAGTTCCTG TACTGGCCAC
    ValGlySerGln AlaLeuVal AspArgIle ArgLeuGlnGly LeuLysAsp MetThrGly
```

FIG. 1D

```
         790        800        810        820        830        840
          *          *          *          *          *          *
CGGTGCTCTC GCCCCATGAC GCCGCACTGT TGATGCGCGG CATCAAGACC CTCAACCTGC
GCCACGAGAG CGGGGTACTG CGGCGTGACA ACTACGCGCC GTAGTTCTGG GAGTTGGACG
AlaValLeuSer ProHisAsp AlaAlaLeu LeuMetArgGly IleLysThr LeuAsnLeu 850        860        870        880        890        900
          *          *          *          *          *          *
GCATGGACCG CCACTGCGCC AACGCTCAGG TGCTGGCCGA GTTCCTCGCC CGGCAGCCGC
CGTACCTGGC GGTGACGCGG TTGCGAGTCC ACGACCGGCT CAAGGAGCGG GCCGTCGGCG
ArgMetAspArg HisCysAla AsnAlaGln ValLeuAlaGlu PheLeuAla TrpGlnPro 910        920        930        940        950        960
          *          *          *          *          *          *
AGGTGGAGCT GATCCATTAC CCGGGCCTGG CGAGCTTCCC GCAGTACACC CTGGCCCGCC
TCCACCTCGA CTAGTAATG GGCCCGGACC GCTCGAAGGG CGTCATGTGG GACCGGGCGG
GlnValGluLeu IleHisTyr ProGlyLeu AlaSerPhePro GlnTyrThr LeuAlaArg 970        980        990       1000       1010       1020
          *          *          *          *          *          *
AGCAGATGAG CCAGCCGGGC GGCATGATCG CCTTCGAACT CAAGGGCGGC ATCGGTGCCG
TCGTCTACTC GGTCGGCCCG CCGTACTAGC GGAAGCTTGA GTTCCCGCCG TAGCCACGGC
GlnGlnMetSer GlnProGly GlyMetIle AlaPheGluLeu LysGlyGly IleGlyAla 1030       1040       1050       1060       1070       1080
          *          *          *          *          *          *
GGCGGCGGTT CATGAACGCC CTGCAACTGT TCAGCCGCGC GGTGAGCCTG GGCGATGCCG
CCGCCGCCAA GTACTTGCGG GACGTTGACA AGTCGGCGCG CCACTCGGAC CCGCTACGGC
```

FIG. 1E

```
              GlyTrpTrpPhe MetAsnAla LeuGlnLeu PheSerArgAla ValSerLeu GlyAspAla
           1090       1100       1110       1120       1130       1140
             *          *          *          *          *          *
       AGTCGCTGGC GCAGCACCCG GCAAGCATGA CTCATTCCAG CTATACCCCA GAGGAGCGTG
       TCAGCGACCG CGTCGTGGGC CGTTCGTACT GAGTAAGGTC GATATGGGGT CTCCTCGCAC
       GluSerLeuAla GlnHisPro AlaSerMet ThrHisSerSer TyrThrPro GluGluArg 1150       1160       1170       1180       1190       1200
             *          *          *          *          *          *
       CGCATTACGG CATTCCGAG GGCTGGTGC GGTTGTCGGT GGGGCTGGAA GACATCGACG
       GCGTAATGCC GTAGAGGCTC CCGACCACG CCAACAGCCA CCCCGACCTT CTGTAGCTGC
       AlaHisTyrGly IleSerGlu GlyLeuVal TrpLeuSerVal GlyLeuGlu AspIleAsp 1210       1220       1230       1240       1250       1260
             *          *          *          *          *          *
       ACCTGCTGGC CGATGTGCAA CAGGCACTCA AGGCGAGTGC CTGAACCCGT CACGGATGAG
       TGGACGACCG GCTACACGTT GTCCGTGAGT TCCGCTCACG GACTTGGGCA GTGCCTACTC
       AspLeuLeuAla AspValGln GlnAlaLeu LysAlaSerAla 1270       1280       1290       1300       1310       1320
             *          *          *          *          *          *
       GTCAATGCAA TGGTGGCAAT GATGAACCTT GTGCCTGGCG ACGGCGTGCC CGGTGACAGC
       CAGTTACGTT ACCACCGTTA CTACTTGGAA CACGGACCGC TGCCGCACGG GCCACTGTCG 1330       1340       1350       1360
             *          *          *          *
       GACCCTGGCG AAACTGCAGA GTGGCTGGAG GCGCTGGAGT CGACCCTGG
       CTGGGACCGC TTTGACGTCT CACCGACCTC CGCGACCTCA GCTGGGACC
```

FIG. 3

PURIFICATION OF rMETase (pAC-1 CLONE)

| PROCEDURE<br>(BATCH 11) | VOLUME<br>(ml) | ACTIVITY<br>(units) | PROTEIN<br>(g) | SA *<br>(units/mg) | RECOVERY<br>RATE (%) | YIELD<br>(%) |
|---|---|---|---|---|---|---|
| CELL LYSIS | 5,000 | 82,000 | 29.3 | 2.8 | 100 | 100 |
| HEAT & UF** | 4,500 | 77,000 | 19.3 | 4.0 | 94 | 94 |
| DEAE-FF.1 | 2,200 | 65,400 | 6.0 | 10.9 | 85 | 80 |
| DEAE-FF.2 | 800 | 57,500 | 2.88 | 20.0 | 88 | 70 |
| ACTICLEAN & CONCENTRATION | 182 | 52,000 | 2.59 | 20.1 | 90 | 63 |

* S.A. : SPECIFIC ACTIVITY.   ** UF : ULTRAFILTRATION

FIG. 18

TOXICITY OF METHIONINASE
(CLINICAL PHASE I TRIAL)

| PHYSICAL & LABORATORY EXAMINATION | GRADE | | |
|---|---|---|---|
| | PATIENT 1 | PATIENT 2 | PATIENT 3 |
| HEMATOLOGICAL | 0 | 0 | 0 |
| GASTROINTESTINAL | 0 | 0 | 0 |
| RENAL | 0 | 0 | 0 |
| PULMONARY | 0 | 0 | 0 |
| FEVER | 0 | 0 | 0 |
| ALLERGIC | 0 | 0 | 0 |
| PHLEBITIS | 0 | 0 | 0 |
| CUTANEOUS | 0 | 0 | 0 |
| CARDIAC | 0 | 0 | 0 |
| NEUROLOGICAL | 0 | 0 | 0 |

* ACCORDING TO WHO TOXICITY CRITERIA

METHIONINASE FORMULATIONS

RELATED APPLICATIONS

This application is a divisional of prior application Ser. No. 08/642,541, filed 3 May 1996, pending which application is a continuation-in-part of U.S. Ser. No. 08/486,519, filed Jun. 7, 1995, now U.S. Pat. No. 5,715,835, U.S. Ser. No. 08/424,300, filed Apr. 24, 1995, now U.S. Pat. No. 5,690,929, and PCT application No. PCT/US93/11311, filed Nov. 19, 1993, which are continuation-in-part applications of U.S. Ser. No. 07/979,165, filed Nov. 19, 1992, now abandoned, all of which are incorporated by reference (including drawings).

TECHNICAL FIELD

The present invention relates to expression modules that encode and express high levels of recombinant methioninase, recombinant methioninase produced using high-level expression modules, compositions containing recombinant methioninase produced using high-level expression modules, methods for purifying recombinant methioninase produced using high-level expression modules, chemically modified forms of recombinant methioninase, and methods of using recombinant methioninase produced using high-level expression modules in antimethionine and antihomocysteine therapy.

BACKGROUND

Therapeutic drug-based treatment of cancer is directed at the use of medicinals which selectively inhibit or kill the cancer cells while not harming normal tissue function beyond acceptable amounts. The difficulty with conventional chemotherapy has been the toxicity of therapeutic drugs for normal tissue.

Many tumors have been shown to have absolute requirement for methionine in a variety of cell types and evaluated tumor tissues, including tumors of the colon, breast prostate, ovary, kidney, larynx melanoma, sarcoma, lung, brain, stomach and bladder as well as leukemias and lymphomas. Methionine dependence has been defined as an inability of tumors to grow when methionine is replaced by homocysteine in the growth medium. See, for example, Chello et al., *Cancer Res.*, 33:1898–1904, 1973; and Hoffman, *Anticancer Res.*, 5:1–30, 1985.

Methionine depletion has been shown to selectively synchronize methionine-dependent tumor cells into late S/$G_2$ phase of the cell cycle. Hoffman et al, *Proc. Natl. Acad. Sci. USA*, 77:7306–7310, 1980. Using the combination of methionine deprivation, followed by repletion of methionine coupled with exposure to an antimitotic agent, termed antimethionine chemotherapy, tumor cells have been selectively eliminated from cocultures of normal and tumor cells, resulting in cultures of normal cells proliferating vigorously. Stern et al., *J. Natl. Cancer Inst.*, 76:629–639, 1986.

However, in order for methionine-dependent chemotherapy to be conducted in vivo, it is necessary to have a means to effectively deplete serum of circulating methionine. Methionine depletion methods have not been described that reduce circulating methionione levels in vivo in a manner sufficient to be effective in antitumor therapies.

Methioninase, an enzyme which degrades methionine, has been purified from a variety of bacterial sources, and has been reported to slow the rate of tumor cell proliferation in vitro. Kreis et al., *Cancer Res.*, 33:1862–1865, and 1866–1869, 1973; Tanaka et al., *FEBS Letters*, 66:307–311 1976; Ito et al., *J. Biochem.* 79:1263–1272, 1976; and Nakayama et al., *Agric. Biol. Chem.* 48:2367–2369, 1984.

Kreis et al., *Cancer Res.* 33:1866–1869, 1973, have described the use of highly impure methioninase preparations isolated from *Clostridium sporgenes* at 1150 units/kg/day to inhibit growth of carcinosarcoma cells implanted in a mouse model. Although the enzyme apparently reduced primary tumor cell growth, it was not reported to reduce the T/C (treated versus control) ratio of tumor diameter below 50%, and was not reported to have any effect on metastasis. The authors also indicated that tumor specificity of the methioninase cannot be expected without other unspecified interventions, and further do not comment on the possibly that endotoxin, or other components of the impure preparation, were responsible for the effects observed. The only toxicity studies reported were absence of animal body weight loss after the duration of the treatment, and negative gross examination for toxicity. Further, the authors report that the enzyme had a serum half life of 4 hours.

Kreis et al., *Cancer Res.* 33:1866–1869, 1973, further reported the use of a methionine-free diet as a means to deplete methionine as an antitumor therapy. However, the authors reported that the diet did not slow tumor growth as effectively as the use of an impure preparation of methioninase and resulted in the undesirable side effect of continuous loss of weight of the animal. The authors did not report the use of methionine deficient diets combined with methioninase treatment, and did not study cell synchronization.

The priority applications of the present invention disclose effective chemotherapy of tumors directed at effectively reducing the amount of methionine as to provide a beneficial antitumor effect without deleterious injury using methioninase. The present invention improves the disclosed therapeutic and diagnostic methods and composition by providing a source for producing commercially viable quantities of highly pure recombinant methioninase.

BRIEF DESCRIPTION OF THE INVENTION

The present invention is based, in part, on the generation of high-level expression modules encoding methioninase. The expression modules of the present invention produce recombinant methioninase in an appropriate host cell, such as *E. coli*, at levels ranging from about 5–75% of total cellular protein.

Based on this observation, the invention provides high expression modules encoding methioninase that expresses unexpectedly high levels of recombinant methioninase. High expression modules, such as those utilizing the T7 RNA polymerase promoter, have been used to produce recombinant methioninase at about 1 to 4 gram/liter with a specific activity of about 2 to 4 units/mg, before purification, using appropriate incubation conditions and purification methods.

The invention further provides methods of accurately selecting transformants containing high-level expression modules encoding methioninase for the ability to produce high levels of recombinant methioninase. Such procedures can be used to specifically select transformants containing recombinant methioninase-encoding DNA molecules isolated from an organism that naturally produces methioninase, as well as to identify transformants that express altered forms of a recombinant methioninase-encoding DNA molecule that increases the level of expression in a given host or the activity of the recombinant methioninase produced.

The invention further provides methods of producing recombinant methioninase using cells containing high-level expression modules encoding methioninase.

The present invention further provides methods of purifying methioninase to obtain a highly pure, endotoxin free methioninase.

The invention further provides substantially pure recombinant methioninase produced using cells containing high-level expression modules encoding methioninase.

The present invention further provides methioninase in crystallized form.

The invention further provides compositions for diagnostic and therapeutic use that contain recombinant methioninase produced using a high-level expression module encoding methioninase.

The invention further provides methods for inhibiting tumor cell growth using the recombinant methioninase of the present invention.

The invention further provides the recombinant methioninase of the present invention in chemically modified forms, such as by coupling of the recombinant methioninase to polymers such as polyethylene glycol (PEG).

The recombinant methioninase of the present invention can further be used to lower homocysteine levels in patients to reduce the risk of, and to treat, cardiovascular diseases.

The recombinant methioninase of the present invention can further be used to deplete methionine for tumor diagnosis and imaging.

Other features, advantages and related embodiments of the present invention will be apparent based on the disclosures contained herein.

BRIEF DESCRIPTION OF THE DRAWINGS

FIG. 1 (SEQ ID NOS: 1 through 3), panels a–c, provides the nucleotide (and corresponding amino acid sequence) of a methioninase encoding DNA molecule isolated from P. putida.

FIG. 3 provides an overview of typical purity and recovery yields for rMETase.

FIG. 18 provides a toxicity evaluation of methioninase in a human patients.

Figure 2:
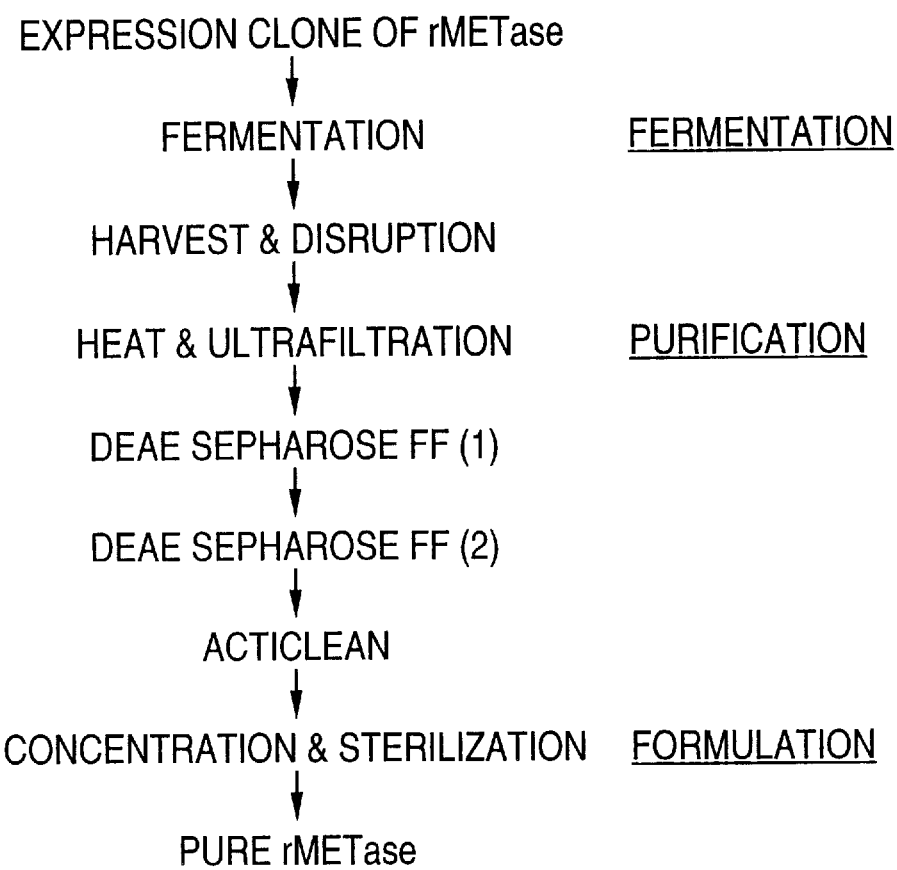
FIG. 2 provides an outline of the purification steps used to obtain highly pure, endotoxin free methioninase.

The drawings are not necessarily to scale, and certain features of the invention may be exaggerated in scale and shown in schematic form in the interest of clarity and conciseness.

DESCRIPTION OF THE INVENTION

A. Definitions

"Amino acid residue" refers to an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.* 243:3552–59, 1969, and adopted at 37 CFR 1.822(b)(2)), hereby incorporated by reference.

| TABLE OF CORRESPONDENCE | | |
|---|---|---|
| SYMBOL 1-Letter | AMINO ACID 3-Letter | |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as NH2 or acetyl or to a carboxy-terminal group such as COOH.

"Recombinant DNA (rDNA) molecule" refers to a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

"Vector" refers to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow convenient expression of a recombinant methioninase protein of this invention.

B. DNA Segments and Vectors

1. Methioninase-Coding DNA Molecules

It has been found that by operably linking an isolated DNA molecule encoding methioninase to a promoter, particularly an RNA polymerase promoter such as the T7 RNA polymerase promoter, recombinant methioninase can be expressed at levels from about 5–75% of total cellular protein, when introduced into an appropriate host cell. Accordingly, the invention provides high-level expression modules that express high levels of recombinant methioninase when introduced into a host under appropriate conditions.

As used herein, a high-level expression module, or an expression module of the present invention, refers to a nucleic acid molecule that contains one or more expression control elements that direct the transcription and translation of an operably linked nucleotide sequence that encodes methioninase. The expression module can be an isolated nucleic acid molecule or can be present in a vector (described below).

The expression modules of the present invention contain control elements that direct the production of recombinant methioninase such that the recombinant methioninase produced represents from about 5–75% of total cellular protein, preferably more than 10% of total cellular protein. The preferred expression control elements are RNA polymerase promoters, the most preferred being the T7 RNA polymerase promoter. Other examples of RNA polymerase promoters include, but are not limited to, the Tac and Trc promoters.

A promoter is an expression control element formed by a DNA sequence that permits binding of RNA polymerase and transcription to occur. Promoter sequences compatible with a particular hosts system are known in the art and are typically provided in a plasmid vector containing one or more convenient restriction sites. Typical of such plasmids vectors are those containing the T7 RNA polymerase promoter, pT7 and pET that are available from a variety of sources such as commercial suppliers and the American Type Culture Collection.

The expression modules of the present invention further comprise a nucleic acid sequence that encodes methioninase. As used herein, a nucleic acid sequence is said to encode methioninase when the transcription and translation of the nucleic acid molecule comprising the sequence results in the production of a protein having methioninase activity.

L-Methioninase (L-methionine-alpha-deamino-gammamercaptomethane-lyase or methioninase) is an enzyme that degrades methionine by deamination and dethiomethylation. Methioninase activity can be measured at least by measuring the amount of alpha-ketobutyrate formed upon cleavage of methionine. One unit (U) of methioninase is defined as an amount of enzyme that produces 1 micromole of alpha-ketobutyrate per minute from methionine under the standard assay conditions described by Ito et al., *J. Biochem.*, 79:1263–1272, 1976; and Soda, *Analyt. Biochem.* 25:228–235, 1968.

The methioninase-encoding nucleic acid sequence can comprise an unaltered sequence obtained from an organism that naturally produces recombinant methioninase, or can comprise a sequence obtained from an organism that naturally produces methioninase that has been altered to contain one or more nucleic acid or amino acid substitutions, deletions or additions.

The methioninase-encoding nucleic acid molecule, whether altered or unaltered, can be derived from any organism that naturally produces methioninase. The preferred source of the methioninase-encoding nucleic acid molecule is *Pseudomonas putida*. Example 1 discloses the isolation and sequencing of a methioninase-encoding nucleic acid molecule from *P. putida*. Other preferred sources for a methioninase-encoding nucleic acid molecule include, but are not limited to, *Trichomonas vaginalis*, *Nippostrongylus brasiliensis*, and *Fusobacterium sp*.

The complete coding sequence for methioninase can be obtained from a variety of sources, especially those recited above, using a variety of methods. The isolation of methioninase-encoding nucleic acid molecules from an organism other than *P. putida* is greatly facilitated by the amino acid and nucleic acid sequences provided in SEQ ID NO:1.

Specifically, a skilled artisan can readily use the nucleic acid sequence provided in Seq. ID NO:1 to prepare pairs of oligonucleotide primers for use in a polymerase chain reaction (PCR) to selectively amplify a methioninase-encoding nucleic acid molecule from methionine expressing organisms. The preferred PCR primer pairs based on the sequence provided in SEQ ID NO:1 are:

5'-GCCGGTCTGTGGAATAAGCT-3' (Sense) SEQ ID NO:4

5'-CCAGGGTCGACTCCAGCGCC-3' (Antisense) SEQ ID NO:5

A preferred PCR denature/anneal/extend cycle for using the above PCR primers is as follows: first denaturation at 95° C. for 10 minutes, then 5 cycles of denaturation at 94° C. for 30 seconds, annealing at 60° C. for 30 seconds, and extension at 72° C. for 2 minutes; then 25 cycles of denaturation at 94° C. for 30 seconds, 60° C. for 30 seconds, then extension at 72° C. for 1.5 minutes; then final extension at 72° C. for 10 minutes. The PCR amplified products are two bands of which the 1365 bp band was collected, and purified as the insert ONCase-1 DNA.

Alternatively, a fragment of the nucleotide sequence or SEQ. ID No. 1 can be used as a probe to isolate DNA encoding methioninase from organisms other than *Pseudomonas putida* using art-known methods. Oligomers containing approximately 18–20 nucleotides (encoding about a 6–7 amino acid stretch) are prepared and used to probe genomic DNA libraries to obtain hybridization under conditions of sufficient stringency to eliminate false positives using procedures well known in the art. (See Sambrook et al. Molecular Cloning, Cold Spring Harbor Press 1989)

DNA segments (i.e., synthetic oligonucleotides) that are used as probes or specific primers for the polymerase chain reaction (PCR), as well as gene sequences encoding methioninase, can readily be synthesized by chemical techniques, for example, the phosphotriester method of Matteucci, et al., (*J. Am. Chem. Soc.* 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

In addition to PCR and DNA probe based methods, DNA molecules encoding methioninase can be isolated using polyclonal antiserum or monoclonal antibodies raised against peptide fragments of SEQ ID NO:2 that are predicted as being immunogenic. Such antibodies can be used to probe an expression library generated from a given organism, such as a lambda gt11 library, to obtain DNA molecules encoding methioninase from an organism other the *P. putida*.

Once a naturally occurring methioninase-encoding nucleic acid molecule is obtain, a skilled artisan can readily employ random or site specific mutagenesis procedures to alter the methioninase-encoding sequence so as to increase the level of expression or to substitute, add, or delete one or more amino acids from the encoded methioninase.

In one embodiment, the methioninase-encoding sequence is altered so as to increase the level of expression of the recombinant methioninase in a given host cell without changing the amino acid sequence of the encoded methioninase. Increased expression of recombinant methioninase in a particular host can be obtained by altering one or more of the codons present in the nucleic acid molecule so that the resulting codons are ones that are more frequently used by the host organism to encode a particular amino acid. Altering a nucleotide sequence to contain preferred codons can be accomplished using art known procedures such as site directed mutagenesis or by synthesizing a nucleic acid molecule containing the preferred codons.

In addition to alterations that affect expression, methioninase-encoding nucleic acid molecules can be altered so as to facilitate purification of the resulting protein. For example, as disclosed in the Examples, by altering either the amino or carboxy terminus of the recombinant methioninase so as to add a polyhistidine stretch, $Ni^{++}$ sepharose can be used to purify the resulting fusion protein.

The methioninase-encoding sequence can also be altered to introduce changes in the amino acid sequence of the encoded methioninase, so as to add, substitute, or delete one or more amino acid residues. The resulting recombinant methioninase will preferably contain alterations that result in recombinant methioninase with better biological or physiological properties such as increased activity, decreased immunogenicity, or increased serum half life. Such altered forms can be rationally designed or randomly generated.

An alteration is said to be rationally designed when the alteration is specifically chosen based on the amino acid sequence of the starting and resulting proteins and a desired physiological property. For example, one type of rationally designed alteration is to replace hydrophobic amino acids with less hydrophobic residues to increase solubility. The preferred method for generating rationally designed alterations is site direct mutagenesis using a mismatched PCR primer extension method.

Alterations are said to be randomly generated when the alteration is not rationally selected. Random mutagenesis techniques, such as chemical mutagenesis and linker scanning mutagenesis, generate a large variety of random and non-specific alterations in a given protein encoding sequence. Such methods can be used to radically alter the methioninase-encoding nucleic acid molecule.

Altered forms of recombinant methioninase generated in this fashion are then screened for desired properties using a variety of art known methods. The choice of selection method employed will be dependent of the host, vector, and mutagenesis methods employed as well as the properties that are selected for.

The present invention further provides vectors containing one or more of the expression modules of the present invention. Vectors are DNA molecules that are capable of autonomous replication within a host. Vectors can contain an episomal origin of replication derived from a naturally occurring plasmid, a genomic origin of replication, or can be derived from a viral genome. The choice of the vector to which an expression module of the present invention is inserted depends directly, as is well known in the art, on the functional properties desired, e.g., protein expression, and the host cell to be transformed.

In one embodiment, the vector includes a prokaryotic replicon. Prokaryotic replicons such as the ColE1 replicon, are well known in the art and can readily be employed in combination with an expression module of the present invention. In addition, the vector may include a gene encoding a selectable marker such as a drug resistance.

Eukaryotic expression vectors can also be used in combination with an expression module of the present invention. Eukaryotic cell expression vectors are well known in the art and are available from several commercial sources. Typical of such vectors are PSVL and pKSV-10 (Pharmacia), pBPV-1/pML2d (International Biotechnologies, Inc.), pTDT1 (ATCC, #31255), the vector pCDM8 described herein, and the like eucaryotic expression vectors. High level expression vectors can further be generated using insect cell expression systems such as a bacculovirus based vector system.

In general terms, the generation of a high expression module encoding methioninase typically involves the following:

First, a DNA is obtained that encodes methioninase. If the sequence is uninterrupted by introns, as expected from a bacterial source, it is suitable for expression in any host. This sequence may be altered to be in a readily excisable and recoverable form by inserting sequences containing one or more restriction endonuclease sites at regions flanking the methioninase-encoding sequence.

The excised or recovered coding sequence is then placed in operable linkage with a high expression control element, preferably in a replicable expression vector. The expression module or vector is then used to transform a suitable host and the transformed host is cultured under conditions to effect the production of the recombinant methioninase. Optionally the recombinant methioninase is isolated from the medium or from the cells; recovery and purification of the protein may not be necessary in some instances, where some impurities may be tolerated.

Each of the foregoing steps can be done in a variety of ways. For example, the desired coding sequences may be obtained from genomic fragments and used directly in appropriate hosts. The constructions of expression vectors that are operable in a variety of hosts are made using two or more appropriate replicons and control elements. Suitable restriction sites can, if not normally available, be added to the ends of the coding sequence so as to provide an excisable gene to insert into these vectors.

3. Transformed Host Cells Expressing High Levels of Recombinant Methioninase

The present invention further provides host cells transformed with an expression module or vector of the present invention so as to produce from about 5–75% of total cellular protein as recombinant methioninase, preferably more than about 10% of total cellular protein. The host cell can be either a prokaryotic or a eucaryotic host.

Any prokaryotic host can be used to express the high-level methioninase-encoding modules of the present invention. The preferred prokaryotic host is *E. coli*. In the Examples that follow, the DH5α and BL21(DE3) strains of *E. coli* were used.

Preferred eucaryotic host cells include insect cells, yeast cells and mammalian cells, preferably insect cells such as SP6 and vertebrate cells such as those from a mouse, rat, monkey or human fibroblastic cell line. Other preferred eucaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eucaryotic tissue culture cell lines.

Transformation of an appropriate host with a high-level expression recombinant module of the present invention is accomplished by well known methods that typically depend on the type of host and vector used. With regard to transformation of prokaryotic host cells, electroporation or salt treatment of the host cells is preferred, for example, see Cohen et al., *Proc. Natl. Acad. Sci. USA* 69:2110, 1972; and Maniatis et al., *Molecular Cloning, A Laboratory Mammal*, Cold Spring Harbor Laboratory, Cold Spring Harbor, N.Y. (1982).

With regard to transformation of eukaryotic cells, electroporation or the use of a cationic lipid is preferred, for example, see Graham et al., *Virol.* 52:456, 1973; and Wigler et al., *Proc. Natl. Acad. Sci. USA* 76:1373–76, 1979.

Successfully transformed cells, i.e., cells that contain an expression module of the present invention, can be identified by well known techniques. For example, cells resulting from the introduction of an expression module of the present invention can be cloned to produce single colonies. Cells from those colonies can be harvested, lysed and their DNA content examined for the presence of the rDNA using a method such as that described by Southern, *J. Mol. Biol.*, 98:503, 1975, or Berent et al., *Biotech.* 3:208, 1985. However, as described below, the present invention further provides a rapid screening method to identify transformants which express high levels of recombinant methioninase.

4. Identification of Hosts Expressing High Levels of Recombinant Methioninase

The present invention further provides methods of identifying a transformed host cell which produces recombinant methioninase at levels from about 5–75% of total cellular protein. Specifically, it has been observed that transformed host cells expressing from about 5–75% of total cellular protein as recombinant methioninase, have a distinct and observable pink color. This is particularly pronounced when *E. coli* is used as the host.

To identify a transformed host cell expressing high levels of recombinant methioninase, a transformed cell is grown on or in a media under conditions in which the recombinant methioninase is expressed and that allows visual inspection of the growing cells. The growing cells or colonies are examined and selected based on the displaying of a pink color.

A variety of culture/growth conditions can be employed to grow transformed host cells for selection using the present methods. The components of the growth medium will depend on the nutritional requirements of the host/vector system employed and inspection system used to identify the pink color associated with high levels of recombinant methioninase expression and thereby allowing isolation of a high-level expression clone. The preferred medium is a solid medium onto which the transformed host cells can be plated and grown as isolated colonies, each of which is derived from single host. The preferred method of identifying high-level expression clones is visual inspection of growing colonies.

5. Production of Recombinant Methioninase Using a High-level Expression Module

The present invention further provides methods for producing recombinant methioninase. Specifically, recombinant methioninase can be produced at commercially significant levels using a host transformed with one or more of the high-level expression modules of the present invention. Such a transformed host will express recombinant methioninase at a level from about 5–75% of total cellular protein. Using the hosts of the present invention, a skilled artisan can readily produce recombinant methioninase for use in a variety of diagnostic and therapeutic methods using art, known methods.

The preferred method for purifying recombinant methioninase produced using a transformed host containing a high expression module encoding methioninase comprises the steps of:

a) heating an extract of a transformed cell that contains methioninase in aqueous buffers from about 40°–60° C. for about 1–10 min., preferably 50° C. for 1 min.;

b) centrifugation of the heated extract from about 10k to 20 k rpm in a GS-3 rotor (Sorvall, Du Pont) for about 15 min. to 1 hour, preferably at about 13 K rpm for about 30 min. at 4 C.;

c) ultrafiltration of the supernatant using a filter of about 50K to 100K pore size, preferably a Millipore Pre/Scale:TFF PLHK 100K 2.5 ft$^2$ cartridge using a 10 mM potassium phosphate buffer (pH8.3);

d) DEAE ion exchange chromatography in low ionic strength (from about 10–50 mM) KCl in a 10–20 mM potassium phosphate buffer at about pH 7.0–7.6, and collecting fractions containing methioninase eluted in a 40–200 mM KCl gradient, preferably using DEAE-Sepharose FF column;

e) a second DEAE ion exchange chromatography in medium ionic strength (50–100 mM) KCl in a 10–20 mM potassium phosphate buffer at about pH 8.0–8.6, and collecting fractions containing methioninase eluted in a phosphate buffer (pH 8.3) eluted in 100–200 mM KCl, preferably using DEAE-Sepharose FF column; and f) contacting said fractions collected in step (e) with a chromatography medium capable of absorbing endotoxin, and collecting the eluant, thereby removing endotoxin from said eluant to form endotoxin-free methioninase having at least 20 units methioninase activity per milligram protein and from 1–100 ng of endotoxin per mg protein, preferably using an Acticlean® Etox column.

The cell extract is prepared from a host cell that has been altered to express high levels of recombinant methioninase (from about 5–75% of total cellular protein). For bacterial cell extracts, the extracts are generally prepared by first harvesting and washing bacterial cell cultures to form a cell paste/pellet, depending upon whether harvesting is by centrifugation or by hollow fiber filtration, which methods are generally well known.

The cells are then disrupted using conventional means. Preferably the cells are disrupted using a homogenizer, such as a cavitator-type homogenizer, for example, a Microfluidics Corp. Model #HC8000.

The resulting suspension is heated to precipitate selective proteins and other insoluble materials. Typical heating conditions are from about 45°–60° C. for 1–10 minutes. Preferred is a heating step of 50° C. for 1 minute.

The heated extract is centrifuged to remove debris, and the supernatant is filtered and applied to DEAE ion-exchange chromatography medium in two steps as described above. Preferred adsorption and elution conditions are described in the Examples. Any of a variety of DEAE ion exchange column chromatography media can be used in these steps, and the choice of media is not to be construed as limiting. Commercial sources include Pharmacia Fine Chemicals, BioRad, and Sigma.

Thereafter, endotoxin is removed to produce a protein having acceptable levels of endotoxin as recited earlier. The endotoxin removal step can be carried out in any of a variety of means, as are well known, and typically involve contacting the protein in solution with a chromatography medium capable of adsorbing endotoxin, and yielding a chromatography medium eluant which contains endotoxin-free protein. The preferred commercial reagent for use in removing endotoxin is Acticlean® Etox.

C. Therapeutic Compositions

The present invention further provides therapeutic compositions comprising a therapeutically effective amount of substantially isolated recombinant methioninase that is produced using a host transformed with a high-level expression module encoding methioninase.

The compositions of the present invention will preferable contain recombinant methioninase that has a specific activity of about 10 to 50 units (U) per mg protein. Typical preparations of purified recombinant methioninase are described herein having a specific activity of about 16 to 24 U/mg. In the Examples, recombinant methioninase prepared using the expression vector pAC-1 had a specific activity of 20.1 U/mg.

The recombinant methioninase in the compositions of the present invention is preferably substantially isolated. By substantially isolated is meant that the enzyme is at least 90% pure by weight, preferably at least 95% pure, and more preferably at least 99% pure, or essentially homogeneous. A preferred recombinant methioninase is essentially homogeneous when analyzed on electrophoretic media such as polyacrylamide gel electrophoresis (PAGE or SDS-PAGE). Homogeneous on PAGE means only a single detectable band.

The recombinant methioninase used to prepare the compositions of the present invention is preferably substantially free of endotoxins, such as bacterial lipopolysaccharides, due to the undesirable side effects associated with endotoxins when physiologically contacted in a mammal, as by i.v. or i.p. administration. By substantially free is meant less than about 10 nanograms (ng) endotoxin per milligram (mg) recombinant methioninase protein, preferably less than 1 ng endotoxin per mg recombinant methioninase, and more preferably less than 0.1 ng endotoxin per mg recombinant methioninase.

The recombinant methioninase used to prepare the compositions of the present invention is preferably prepared from a gene cloned from P. putida and expressed using a high-level expression vector as herein described.

The recombinant methioninase containing compositions of the present invention may further comprise a physiologically tolerable carrier. As used herein, the terms "pharmaceutically acceptable", "physiologically tolerable" and grammatical variations, both referring to compositions, carriers, diluents and reagents that the materials are capable of administration to or upon a mammal or human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. In addition, a therapeutic amount of recombinant methioninase can be present in a ointment or on a diffusible patch, such as a bandage, as to afford local delivery of the agent.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acide as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein. Exemplary of such additional liquid phases are glycerin, vegetable oils such as cottonseed oil, organic esters such as ethyl oleate, and water-oil emulsions, particularly the liposome compositions described earlier.

A therapeutic composition contains an effective amount of recombinant methioninase, typically an amount of at least 0.1 weight percent of active protein per weight of total therapeutic composition, and preferably is at least about 25 weight percent. A weight percent is a ratio by weight of recombinant methioninase protein to total composition. Thus, for example, 0.1 weight percent is 0.1 grams of recombinant methioninase per 100 grams of total composition.

Insofar as a recombinant methioninase composition can be used in vivo intravascularly, it is contemplated in one embodiment to formulate a therapeutic composition for controlled delivery of the recombinant methioninase, and optionally to shield the recombinant methioninase protein from degradation and other phenomenon which would reduce the serum half-life of therapeutically administered recombinant methioninase.

Thus, in one embodiment, the invention contemplates therapeutic compositions containing delivery vehicles such as polymers, polymeric vehicles, particulates, latexes, coacervates, ion-exchange resins, liposomes, enteric coatings, mediators, bioadhesives, microcapsules, hydrogels, and the like vehicles. Exemplary drug delivery vehicles including liposomes are described at least by Tarcha in "Polymers For Controlled Drug Delivery", CRC Press, Boca Raton, 1990.

D. Chemically Modified Recombinant Methioninase

The present invention further provides the recombinant methioninase of the present invention that is chemically modified, for example by conjugation to a polymer. By "chemically modified" is meant any form of recombinant methioninase that is changed to a form that is different than the recombinant methioninase purified from nature. Preferably, the recombinant methioninase is chemically modified by linking the recombinant methioninase to a polymer or to a polyalkylene oxide. Recombinant methioninase conjugated to a polymer increases the serum half-life and decreases the immunogenicity or antigenicity of the resulting compound.

Examples of polymers and polyalkylene oxide to which proteins may be attached include, but are not limited to, polyethylene glycol, particularly MSC-5000 PEG, polyethylene oxide, polypropylene oxide, copolymers of ethylene oxide, and copolymers of propylene oxide. Methods for chemically modifying proteins alre well known to the art and can readily be used to modify the recombinant methioninase of the present invention, for example, see priority application PCT/US93/11311.

E. Formulations of recombinant methioninase

The present invention further provides methioninase in lyophilized or crystalline form. In detail, it has been observed that methioninase can readily be lyophilized or crystallized using art known methods. The resulting preparation of methioninase, crystallized or lyophilized forms, were found to be highly stable, readily hydratable, and remained highly active following rehydration.

A variety of art known methods can be used to obtain methioninase in crystallized or lyophilized form. In the examples, lyophilization and crystallization of methioninase were performed using a Verdis, Freeze mobile 24, at 100 milifar, −80° C. for 72 hours. A skilled artisan can readily adapt other art known procedures for use in producing lyophilized or crystallized forms of methioninase.

F. Uses for the Recombinant Methioninase of the Present Invention

The recombinant methioninase of the present invention can be used in diagnostic and therapeutic methods that have been developed and described elsewhere that use methioninase purified from a natural sources, see PCT/US93/11311. For example, the recombinant methioninase of the present invention can be used 1) as an antitumor agent in a variety of modalities, such as by depleting methionine from a tumor cell, which are possibly universally methionine dependent, tumor tissue or the circulation of a mammal with cancer, so that the tumor growth will be inhibited 2) to induce cell cycle stasis in tumor cells followed by cell synchronization and the use of antimitotic agents, 3) in combination with antimitotic and cell cycle-specific cytotoxic agents, 4) to deplete cellular methionine prior to labeling with [$^{11}$C] methionine, which can be used in tumor diagnosis and localization, 5) to deplete serum homocysteine to prevent and cure cardiovascular diseases that are mediated by high serum levels of homocysteine. In the Examples that follow, the recombinant methioninase of the present invention was administered to three patients. Infusion dosage of up to 20,000 units, infused over ten hours, had no significant side effects and yielded a depletion of methionine for 10 hours following infusion. A skilled artisan will readily use the recombinant methioninase of the present invention as a substitute for recombinant methioninase derived from other sources in any art-known method of use.

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

EXAMPLE 1

Isolation of Nucleic Acid Molecules Encoding Methioninase PCR Reaction of the Insert of Methioninase Gene Clone Genomic DNA of *Pseudomonas putida* AC-1, derived from ATCC8209, was used as template; the primers used were as follows:

t1: 5'-GCCGGTCTGTGGAATAAGCT-3'   (Sense),   SEQ ID NO:4
          HindIII t2: 5'-CCAGGGTCGACTCCAGCGCC-3'   (Antisense).   SEQ ID NO:5
      Sal I The PCR reaction condition was as follows: first denaturation at 95° C. for 10 minutes, then 5 cycles of denaturation at 94° C. for 30 seconds, annealing at 60° C. for 30 seconds, and extension at 72° C. for 2 minutes; then 25 cycles of denaturation at 94° C. for 30 seconds, 60° C. for 30 seconds, then extension at 72° C. for 1.5 minutes; then final extension at 72° C. for 10 minutes. The PCR amplified products are two bands of which the 1365 bp band was collected, and purified as the insert ONCase-1 DNA.

Cloning and Transformation

The ONCase-1 DNA was ligated with pT7Blue T-vector (Novagen) at the EcoR V T-cloning site. The pONCase-1 DNA was transformed into DH5-α bacterial cells using standard procedures.

DNA Sequencing

DNA sequencing was performed using T7 DNA polymerase and the dideoxy nucleotide termination reaction. The primer walking method was used. [$^{35}$S] dATP was used for labeling. Sequencing reactions were analyzed on 6% polyacrylamide wedge or non-wedge gels containing 8M urea. DNA samples were loaded in the order of ACGT. DNA sequences were analyzed by MacVector. The DNA sequence and corresponding amino acid sequence are provided in FIG. 1.

EXAMPLE 2

High Expression Clones of Recombinant Methioninase PCR Reaction of the Insert for the Methioninase Expression Clone The poNCase-1 clone was used as the template, the primers used are as follows:

t14. 5'-GGAATTCCATATGCACGGCTCCAACAAGC-3'   (Sense)   SEQ ID NO:6
              NdeI -continued t15. 5'-AGTCAT<u>CCTAGG</u>TCACATCATCATCATCATGGCACTCGCCTTGAGTGC-3'
BamHI (Antisense)                                              SEQ ID NO:7 t18. 5'-AGTCAT<u>CCTAGG</u>TCAGGCACTCGCCTTGAGTGC-3' (Antisense)
BamHI                                                          SEQ ID NO:8

The PCR reaction condition was as follows: first denaturation at 95° C. for 10 minutes, then 5 cycles of denaturation at 94° C. for 1 minute, annealing at 56° C. for 1.5 minutes, and extension at 72° C. for 2 minutes; then 20 cycles of denaturation at 94° C. for 30 seconds, 56° C. for 30 seconds, then extension at 72° C. for 1.5 minutes; then final extension at 72° C. for 10 minutes. Two PCR amplified products, ONCase-2 (1238 bp), ONCase-3 (1220 bp) band were collected and purified.

Cloning and Transformation

The DNA of ONCase-2 and ONCase-3 DNA was digested with NdeI and BamHI and ligated with the pT7.7 vector at the NdeI and BamHI cloning sites. The pONCase-2 and pONCase-3 DNA sequences were then transformed into BL21 (DE3) bacterial cells using standard procedures.

Selection of pAC-1 and pAC-2 Clones

The positive clones were selected from Ampicillin-containing plates. After storage at 4° C. for 24 hours, the positive clones which expressed high level of recombinant methioninase had a distinct pink color that allowed their identification and selection. The methioninase expression levels of the positive clones were determined by activity assay. Two high expression clones were selected as the pAC-1 clone which contained ONCase-3 and as the pAC-2 clone which contained ONCase-2.

Construction of pAC-3 Clone and pAC-4 Clone

The tetracycline resistance gene was obtained from pBR322 at the Ava I and Cla I sites. The Ava I end was filled into a blunt end, and was ligated with pAC-1 which was digested-with the BamH I and Cla I restriction enzymes, with the BamH I end filled into a blunt end. Positive clones which became pink after storage at 4° C. for 24 hours were selected from Tetracycline-containing plates. A high expression recombinant methioninase clone was determined by activity assay and named as the pAC-3 clone.

The Tetracycline-resistance gene was also obtained from pBR322 at the Ava I and Hind III sites. The Ava I end was filled into a blunt end, and was ligated with pAC-1 which was digested with the Hind III and Cla I restriction enzymes, with the Cla I end filled into a blunt end. Positive clones which became pink after storage at 4° C. for 24 hours were selected from Tetracycline-containing plates. A high expression recombinant methioninase clone was determined by activity assay and named as the pAC-4 clone. A variety of high level expression clones are provided in Table 1.

TABLE 1 rMETase Expression Clones

| Clone | Vector | Antibiotic Resistance | Promoter | Fusion | Expression* (g/l) |
|---|---|---|---|---|---|
| pAC-1 | pT7.7 | Amp | T7 | — | 1.0 |
| pAC-2 | pT7.7 | Amp | T7 | His. Tag | 0.5 |
| pAC-3 | pT7.7 | Tc | T7 | — | 0.5 |
| pAC-4 | pT7.7 | Tc | T7 | — | 1.0 |

*Expression level in shaking flask (TB medium, 37° C., 400 rpm, 36 hours).

EXAMPLE 3

Fermentation of Recombinant Methioninase Expression Clones

The expression clones of recombinant methioninase were grown in Terrific Broth medium containing either Ampicillin (100 μg/ml) or Tetracycline (10 μg), at 28° C. or 37° C. with 400 rpm shaking in a 6-L flask or fermenter.

EXAMPLE 4

Purification of Recombinant Methioninase

An outline of the purification method is provided in FIGS. 2 and 3.

(1) Pre-column Treatment of the Sample

The bacteria were harvested by centrifugation at 800×g at 4° C. for 10 min. The bacterial pellet is then suspended in extraction solution (20 mM potassium phosphate pH 9.0, 10 μM pyridoxal phosphate and 0.01% β-mercaptoethanol) and disrupted with a cavitator-type homogenizer (Microfluidics Corp. model # HC 8000). Heat treatment of the homogenate is then carried out at 50° C. for one minute. The suspension is centrifuged with an automatic refrigerated centrifuge (SORVALL Superspeed RC 2-B) at 4° C. at 13 k rpm for 30 min. The supernatant is then collected. This step is followed by ultrafiltration by a Millipore Prep/Scale-TFF PLHK 100k 2.5 ft$^2$ cartridge with buffer (10 mM potassium phosphate pH 8.3). The pH is adjusted to 7.2 by ultrafiltration.

(2) Chromatographic Conditions

The first column: DEAE Sepharose FF

Column: XK 100/60, Height: 32 cm, Volume: 2.5 L

Solution: [A] 40 mM potassium chloride, 10 mM potassium phosphate (pH7.2) containing 10 μM pyridoxal phosphate and 0.01% β-mercaptoethanol.

[B] 200 mM potassium chloride, 10 mM potassium phosphate (pH7.2) containing 10 μM pyridoxal phosphate and 0.01% β-mercaptoethanol.

Flow Rate: 5 ml/min.

Sample: About 100–200 g of total protein (10–20 mg/ml) are applied on the first column.

Gradient: [1] Pre-wash with solution A approximately 10 volumes until the OD$_{280}$ drops below 0.1.

[2] Gradient: Solution B from 20–100%.

Fractions: Elution fractions of 200 ml are collected. The fractions containing rMETase are identified by activity assay and pooled.

The Second Column: DEAE Sepharose FF

Column: XK 50/30, Height: 25 cm, Volume: 500 ml

Solution: [A] 100 mM potassium chloride, 10 mM potassium phosphate (pH8.3) containing 10 μM pyridoxal phosphate and 0.01% β-mercaptoethanol.

[B] 200 mM potassium chloride, 10 mM potassium phosphate (pH8.3) containing 10 μM pyridoxal phosphate and 0.01% β-mercaptoethanol.

Flow Rate: 5 ml/min.

Sample: Approximately 10–20 g of total protein (2–4 mg/ml), after dialysis in 100 mM potassium chloride, 10 mM potassium phosphate (pH8.3) containing 10 μM pyridoxal phosphate for 24 hours, are applied on the second column.

Gradient: [1] Pre-wash with solution A approximately 5 volumes until the $OD_{280}$ drops below 0.05.

[2] Gradient: Solution B from 0%–60%.

Fractions: Elution fractions of 200 ml are collected. The fractions containing rMETase are identified by the activity assay and pooled.

The Third Column: Sephacryl S-200 HR

Column: HiPrep 26/60, volume 320 ml.

Solution: 0.15M sodium chloride in 10 mM sodium phosphate (pH7.2)

Flow Rate: 1.2 ml/min.

Sample: Approximately 10 ml concentrated sample. (after dialysis in 0.15M sodium chloride, 10 mM sodium phosphate (pH7.2) for 12 hours), are applied to the third column.

Fractions: Elution fractions of 20 ml containing rMETase, which are identified by yellow color and activity assay, are collected.

The Fourth Column: Acticlean® Etox

Purified rMETase (10–20 mg protein/ml) in a volume of 100–200 ml is applied on a 500 ml Acticlean® Etox column, and eluted with elution buffer (0.15M sodium chloride in 10 mM sodium phosphate pH7.2) in order to eliminate endotoxin. Acticleans Etox is reusable and can be cleaned with 1M sodium hydroxide and can be autoclaved.

Concentration of the Final Eluant

The final eluant is concentrate with 30K Amicon Centriprep Concentrators. The formulation for purified rMETase is 0.15M sodium chloride, 10 mM sodium phosphate, pH7.2.

Purification of rMETase.Histidine: Chromatography on $Ni^{++}$ Sepharose Column

The cell homogenate, after pre-column treatment, is suspended in binding buffer (5 mM imidazole, 0.5M NaCl, 20 mM Tris.HCL, pH7.9). The column is then washed with 10 volumes of binding buffer followed by washes with 6 volumes of wash buffer (60 mM imidazole, 0.5M sodium chloride, 20 mM Tris, HCl, pH7.9). Elution occurs after 6 volumes of elution buffer (1M imidazole, 0.5M NaCl, 20 mM Tris. HCl pH7.9) have been run through the column. The fractions containing rMETase, identified by yellow color, are collected.

EXAMPLE 5

Analysis for The Purity of rMETase with HPLC

Column: SUPELCO, 8-08541, Progel TM-TSK, G 3000-SWXL, 30 cm×7.8 mm.

Eluent Solution: 0.15M sodium chloride in 10 mM sodium phosphate buffer (pH7.2).

Flow Rate: 0.1 ml/min.

Sample: 20 µl (0.1–1 mg/ml).

Figure 4:
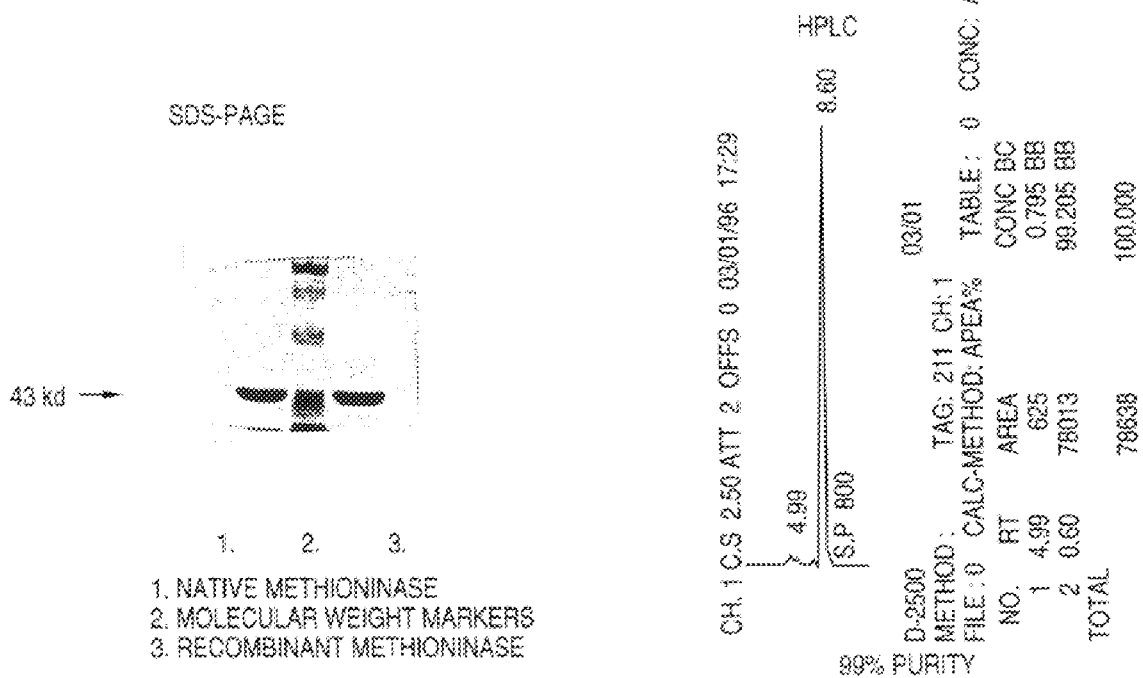
FIG. 4 provides an example of the purity of rMETase produce by the present methods.

An example for production of rMETase is shown in FIGS. 2 and 3. Purity is shown in FIG. 4.

EXAMPLE 6

Figure 5:
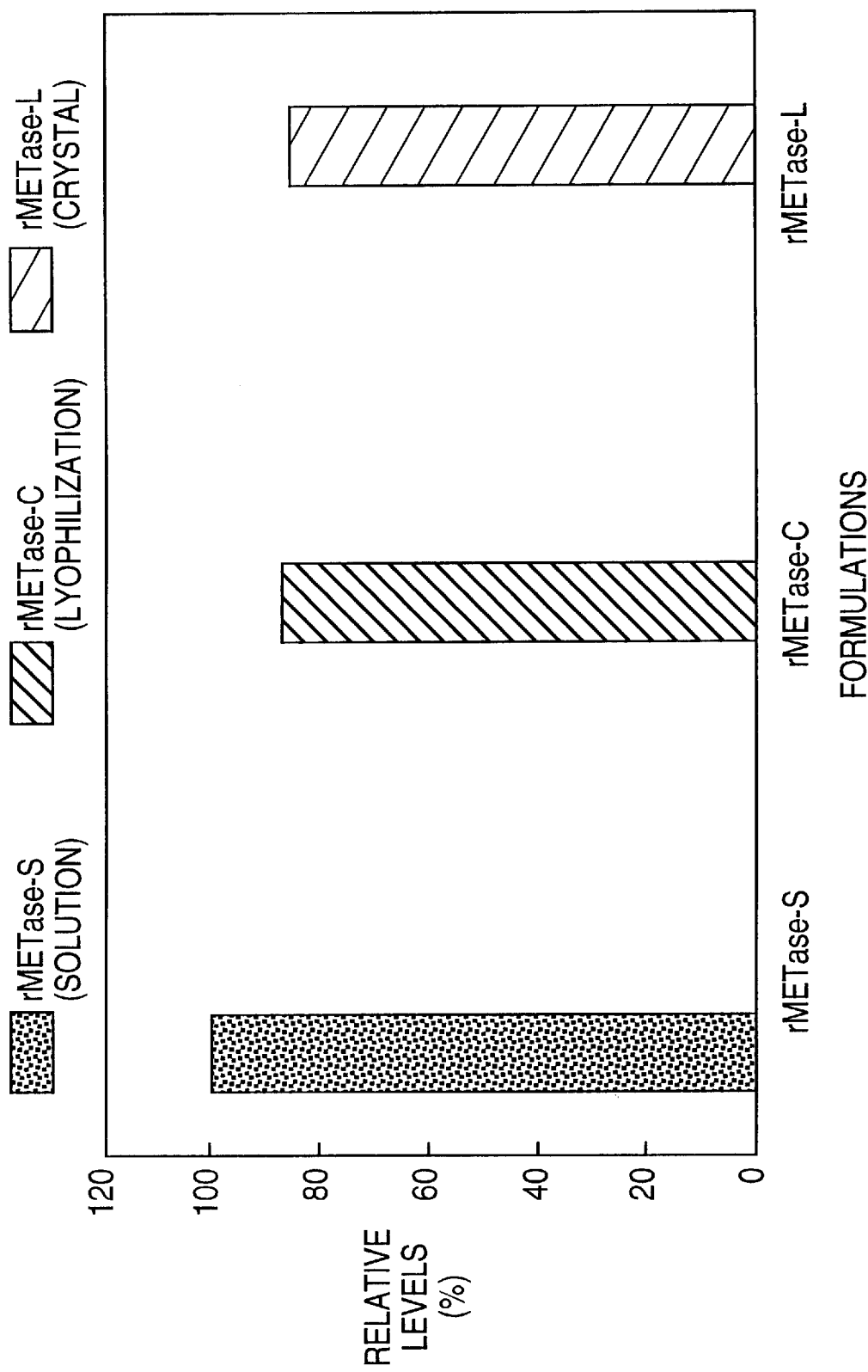
FIG. 5 provides an activity profile for different rMETase formulations.

Formulations Containing Recombinant Methioninase, Crystallized and Lyophilized Forms Solution Formulation:

rMETase is formulated in solution, 0.15M sodium chloride, 10 mM sodium phosphate buffer (pH 7.2), at the concentration 10–20 mg/ml. The stability of rMETase is showed in FIG. 5.

Crystallized Form:

rMETase (10–20 mg/ml), in a 0.15M sodium chloride and 10 mM sodium phosphate buffer (pH 7.2) was desalted using a Sephadex G-25 (DNA grade, superfine, Sigma) column. The solution was frozen on a dry ice and acetone bath and then crystallized in a vacuum of 100 milifar, at −80° C., for 72 hours using a Verdis Freeze Mobil 24.

Lyophilized Form:

rMETase (10–20 mg/ml), in a 0.15M sodium chloride and 10 mM sodium phosphate buffer (pH 7.2), was frozen on a dry ice and acetone bath and lyophilized in a vacuum of 100 milifar, at −80° C., for 72 hours using a Verdis Freeze Mobil 24.

Assay for Activity:

The assay was carried out in a 1 ml volume of 50 mM phosphate buffer pH 8.0, containing 10 µM pyridoxal phosphate and 10 mM methionine for 10 min. at 37° C. with varying amounts of enzyme. The reaction was stopped by adding 0.5 ml of 4.5% TCA. The suspension was centrifuged at 15K rpm for 2 min. 0.5 ml of supernatant with 0.5 ml of 0.05% 3-methyl-2-benzothiazolinone hydrazone in 1 ml of 1M sodium acetate pH 5.2 was incubated at 50° C. for 30 min. And a-Ketobutyrate was then determined by spectrophotometry at $OD_{335}$. The amount of protein was determined by the procedure of Lowry Reagent Kit (Sigma). The specific activity was calculated as units/mg protein.

The activity of rMETase were compared, and the results showed no big difference between different formulations.

EXAMPLE 7

Chemical Modification of Recombinant Methioninase

The purified rMETase was formulated in a 0.15M sodium chloride in 10 mM sodium phosphate buffer (pH 7.2) at a concentration between 0.1M and 0.2M. The activity was approximately 20 units/mg.

M-SC 5000 PEG molecular weight 5000 (Methoxy-SC-PEG, MW 5000 from Shearwater polymers Inc.), was dissolved in 20 mM sodium phosphate buffer (pH 8.3) at a concentration between 2 mM and 20 mM. The molar rations of M-SC 5000 PEG to rMETase are varied from 10:1 to 120:1.

The PEGylation reactions were carried out in reaction buffer (25 mM sodium phosphate buffer, pH 8.3), at 20° C. for 60 minutes. The reactions were stopped with stop buffer (0.14M sodium phosphate buffer, pH 6.5) at 0° C. Unreacted M-SC 5000 PEG was then removed with 30K Amicon Centriprep Concentrators. The resulting PEG-methioninase was formulated in 0.15M sodium chloride and 10 mM sodium phosphate (pH 7.2) while centrifuging with 30k Amicon Centriprep concentrators.

Analysis of PEG-rMETase in vitro

Figure 6:
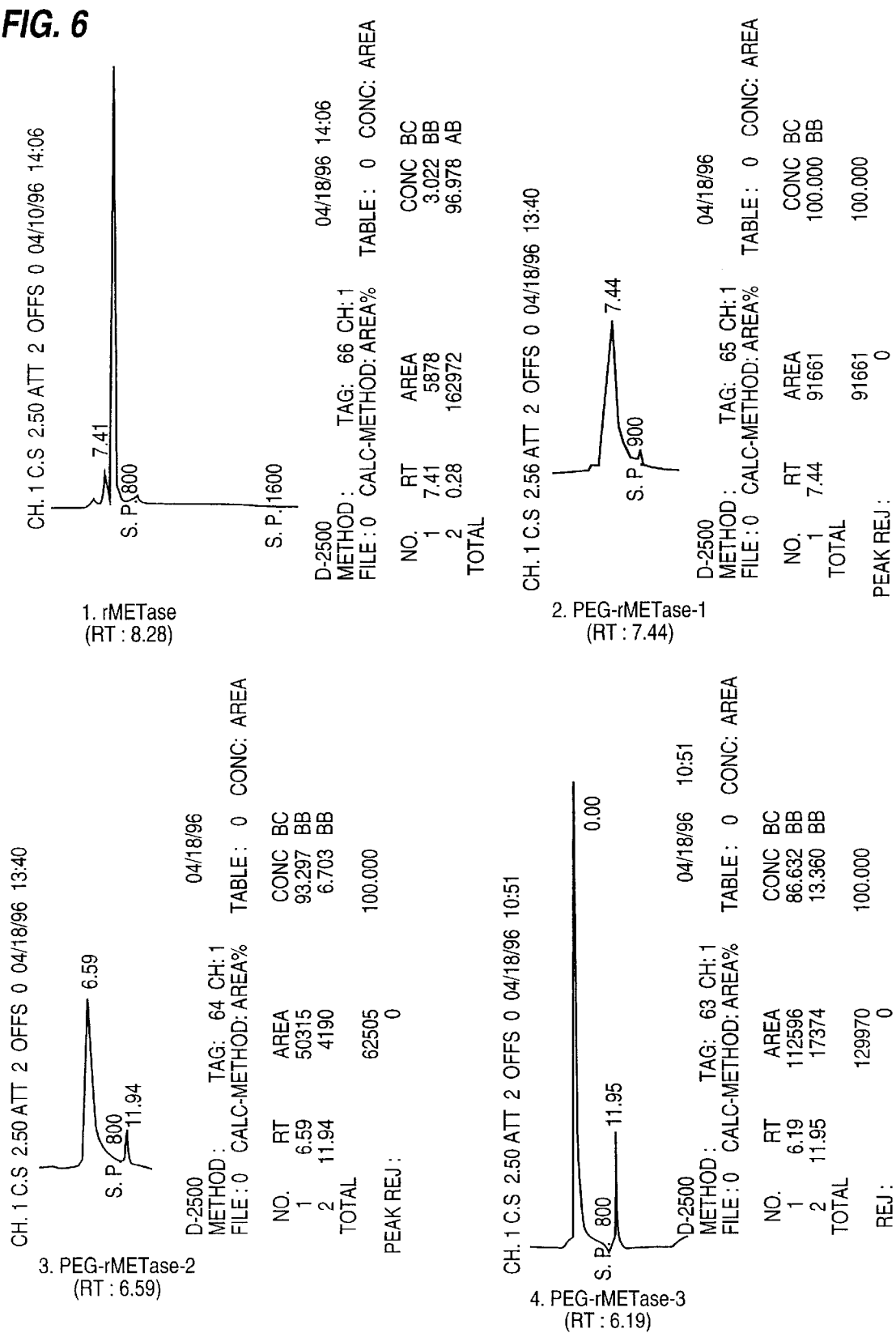
FIG. 6 provides typical purity data for PEG-rMETase.
Figure 7:
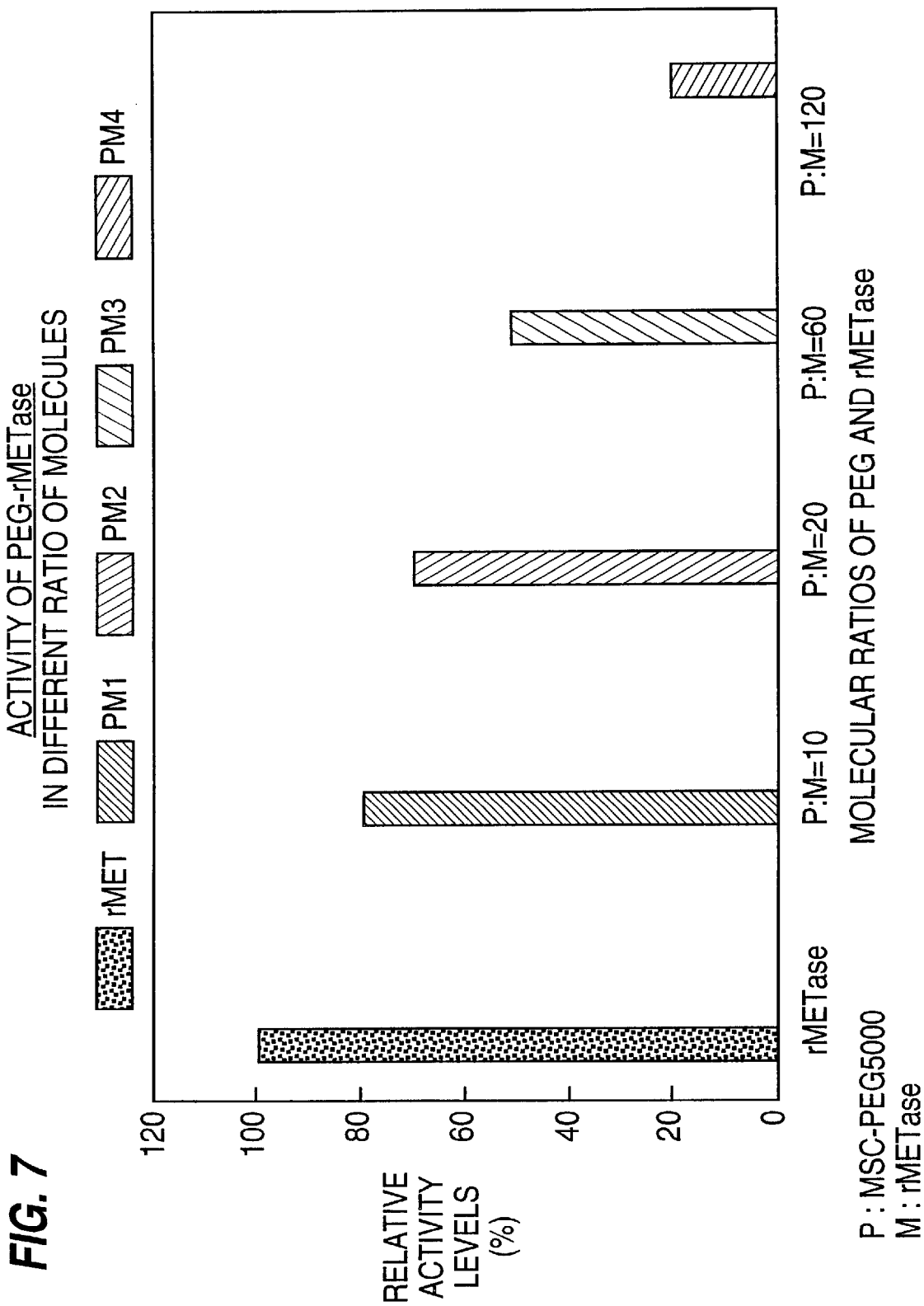
FIG. 7 provides typical activity data for PEG-rMETase.
Figure 8:
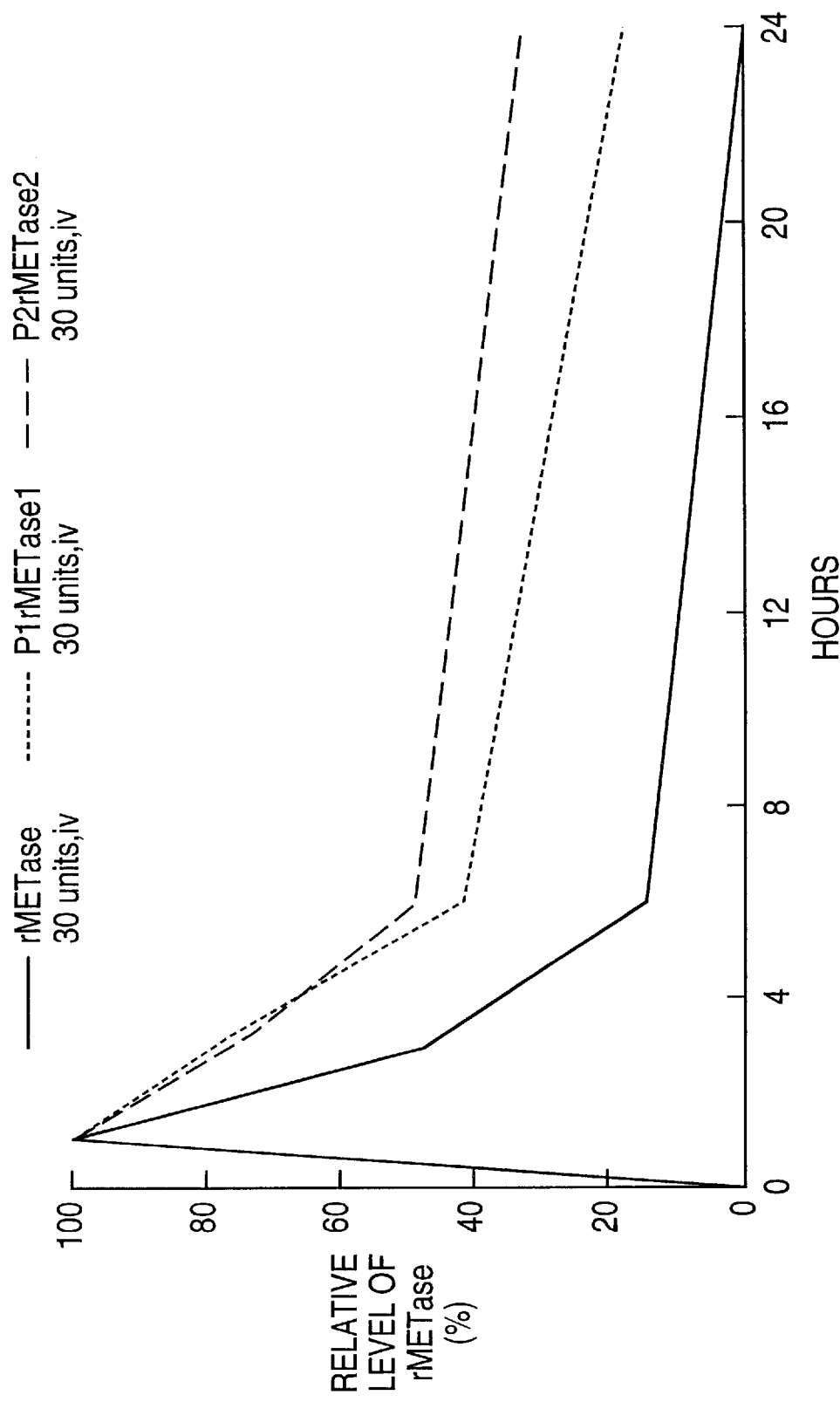
FIG. 8 provides the pharmacokinetics of PEG-rMETase in mice.

PEG-rMETase were analyzed by activity assay, electrophoresis and HPLC, FIGS. 6–8.

Activity Assay

The activity of PEG-rMETase were between 80% to 20% of the unmodified rMETase.

Electrophoresis

PEG-rMETase were applied by both native and SDS-PAGE.

HPLC Analysis:

PEG-rMETase were applied to a gel filtration column, no original rMETase peak was detected, only the PEG-METase peak were observed. The retention time (RT) were shorter along with the molecular ratios of PEG and rMETase increased.

Pharmacokinetics of PEG-rMETase:

Purified endotoxin-free PEG-rMETase were injected into the tail-vein of mice. The blood samples were collected every two hours. The levels of rMETase were measured by activity assay (FIG. 8).

EXAMPLE 8

Efficacy and Toxicity of Recombinant Methioninase

1. Growth Inhibition of KB3-1 Cells by rMETase in vitro

Figure 9:
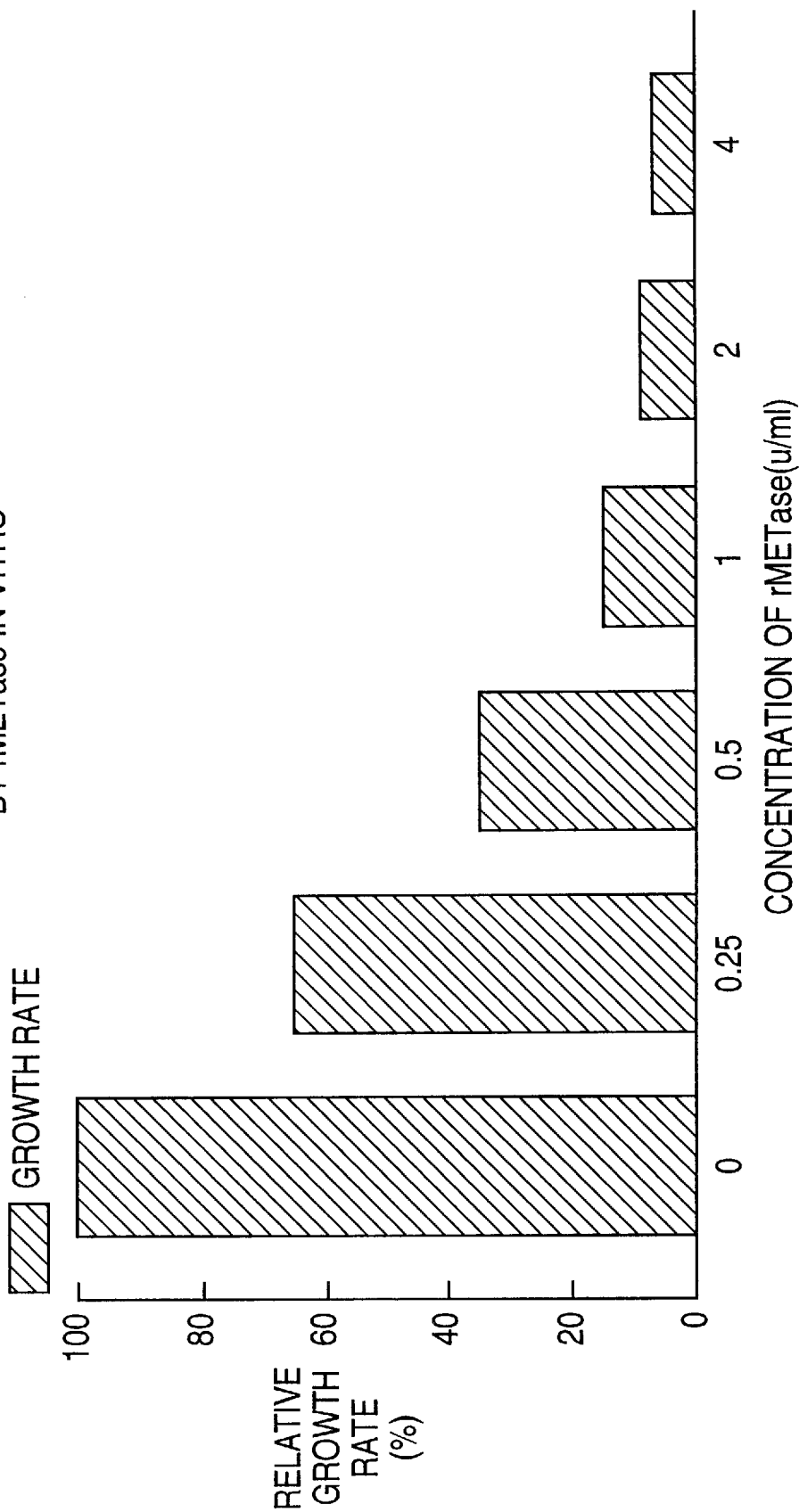
FIG. 9 provides the growth inhibition of KB3-1 cells using rMETase.
Figure 10:
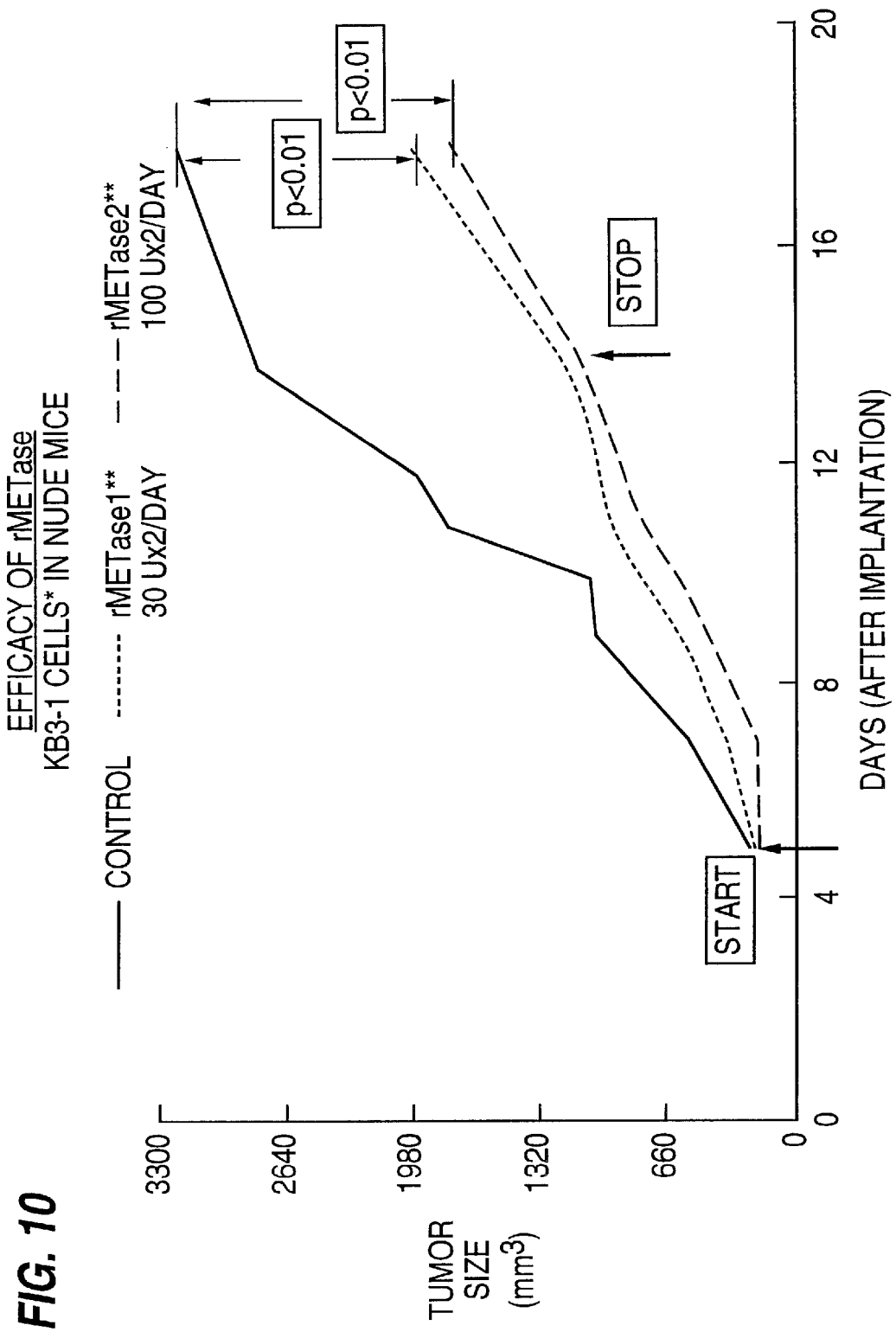
FIG. 10 provides efficacy of rMETase against KB3-1 cells in nude mice.
Figure 11:
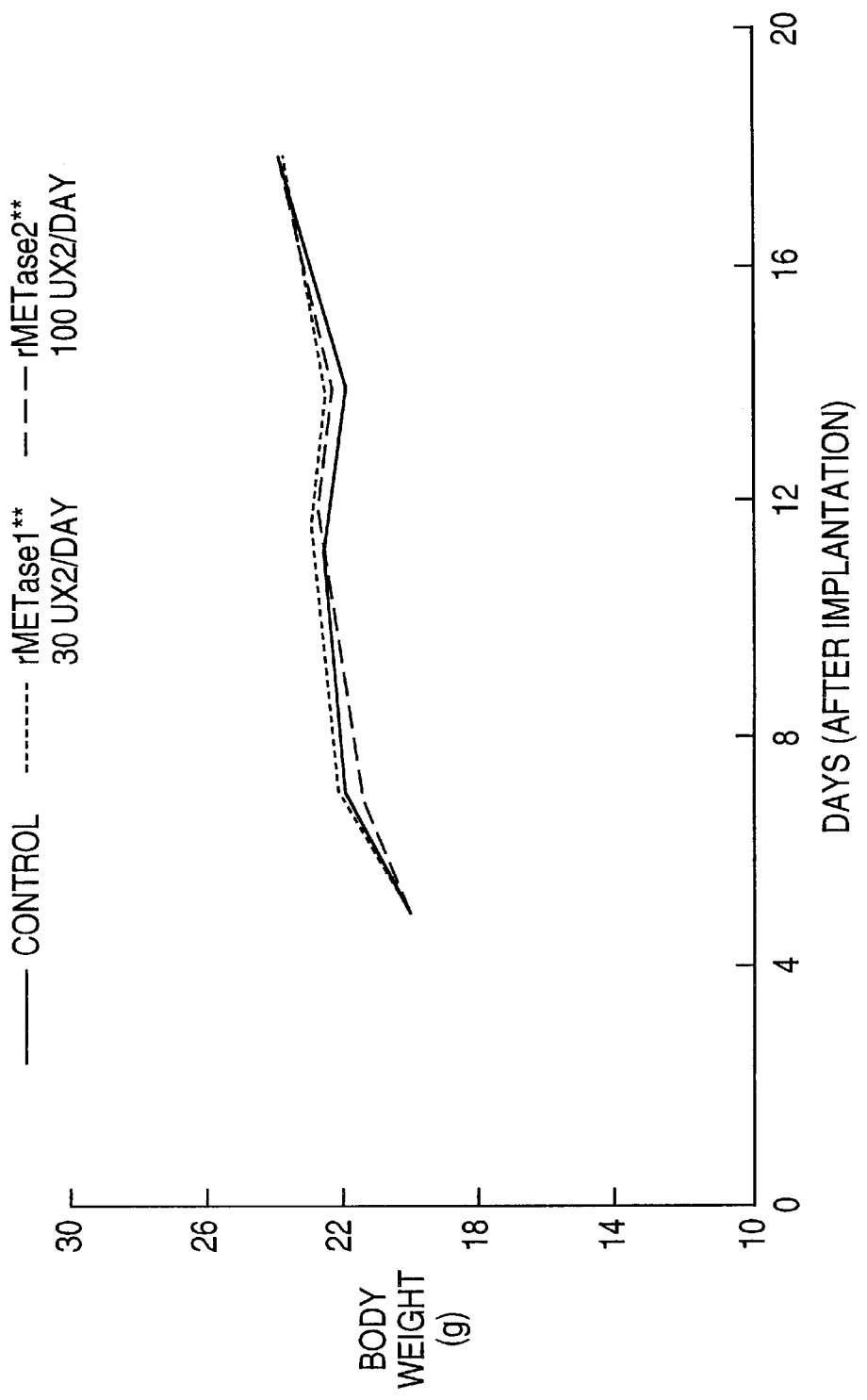
FIG. 11 provides the toxicity of rMETase in nude mice.
Figure 12:
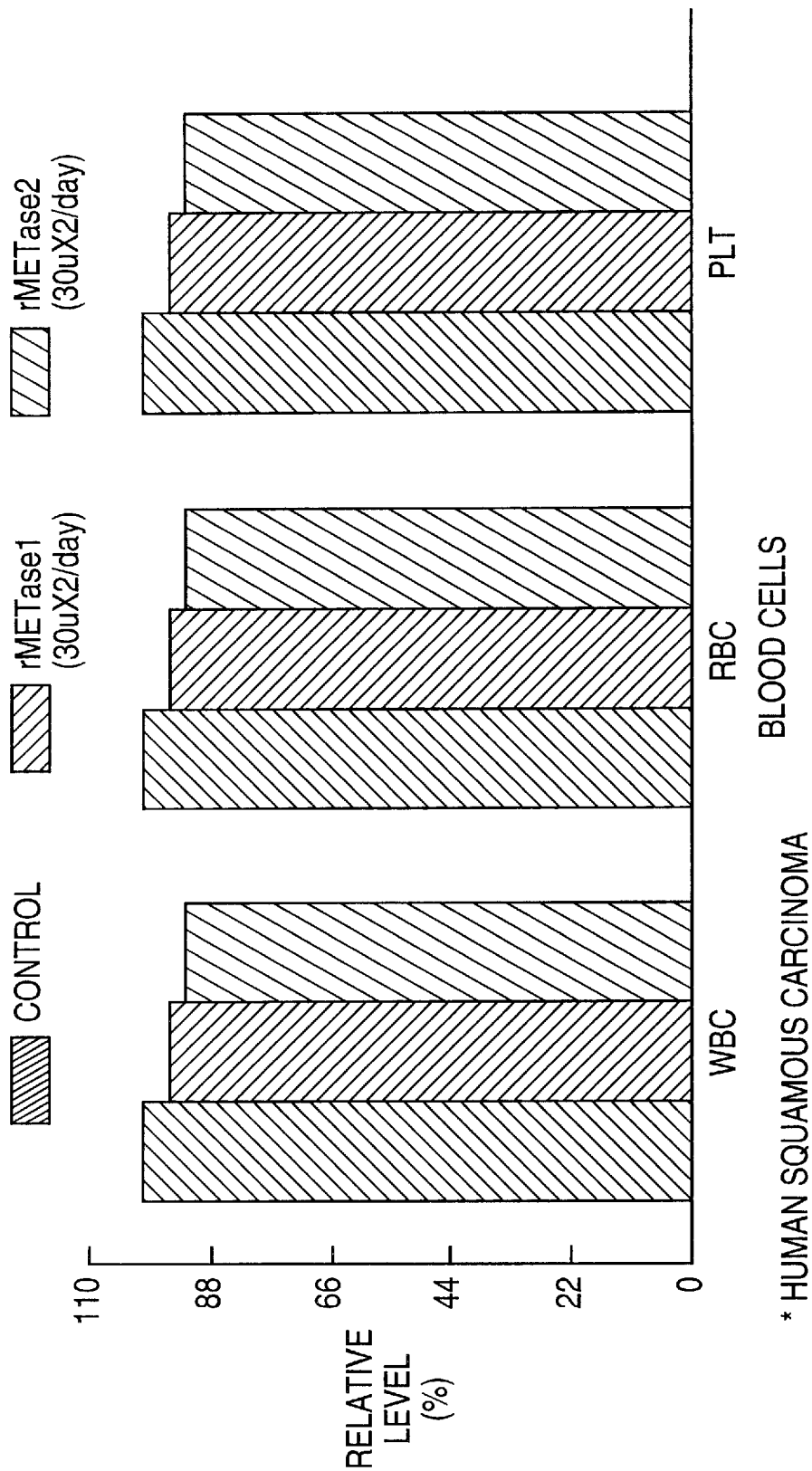
FIG. 12 provides the toxicity of rMETase in nude mice with KB3-1 cells.
Figure 13:
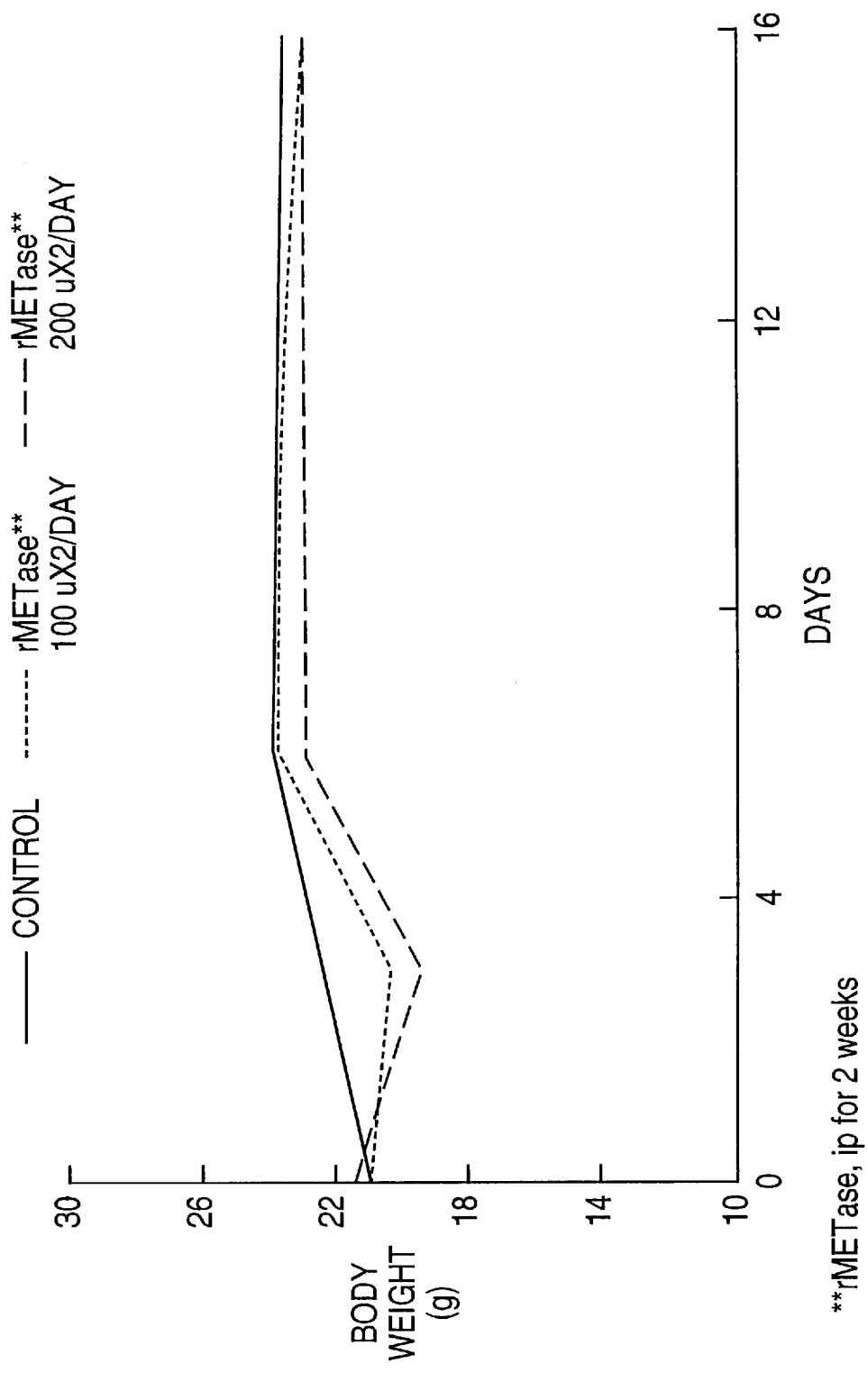
FIG. 13 provides the toxicity of rMETase in BALB/C mice.
Figure 14:
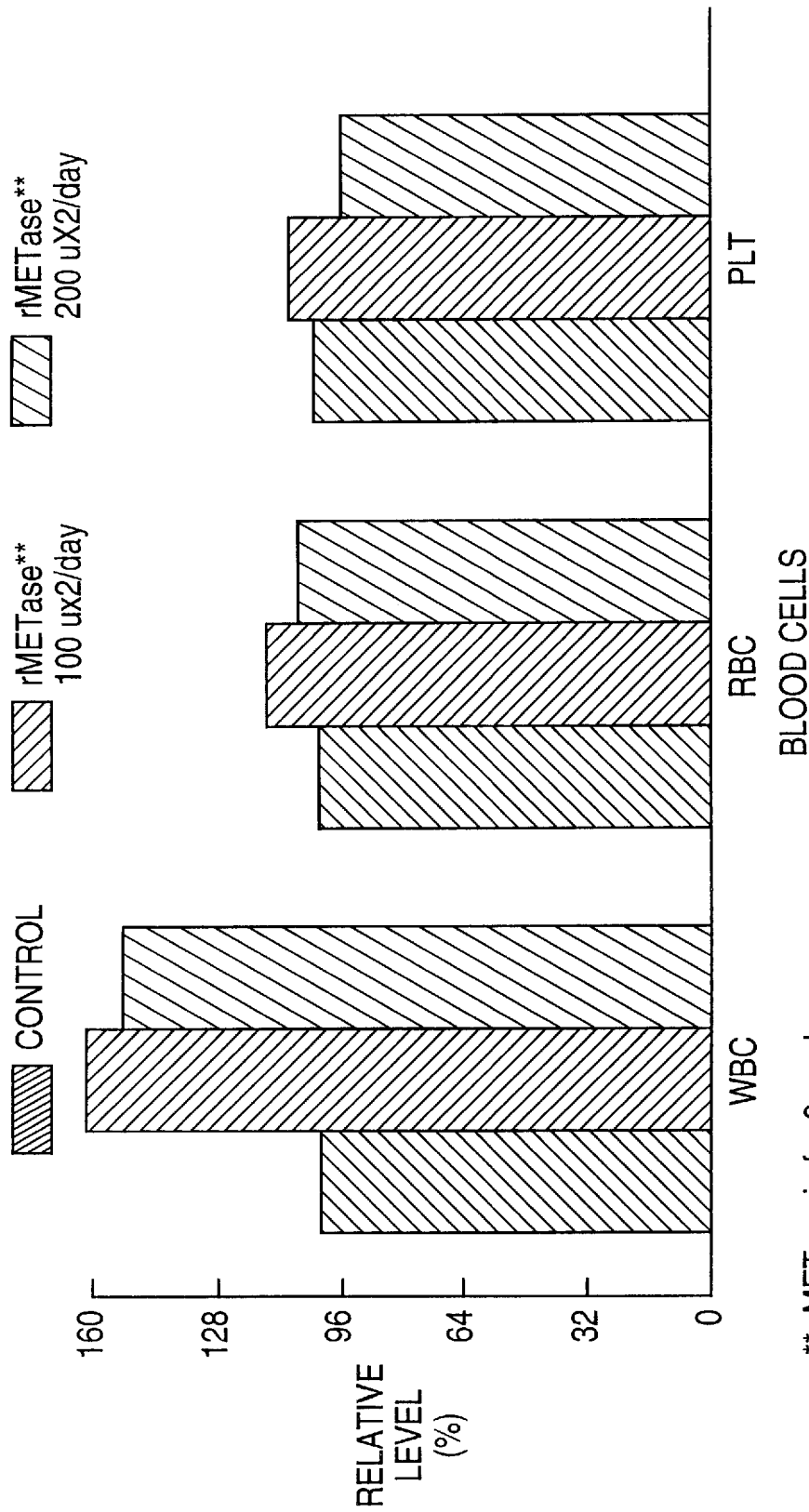
FIG. 14 provides the toxicity of rMETase in BALB/C mice.
Figure 15:
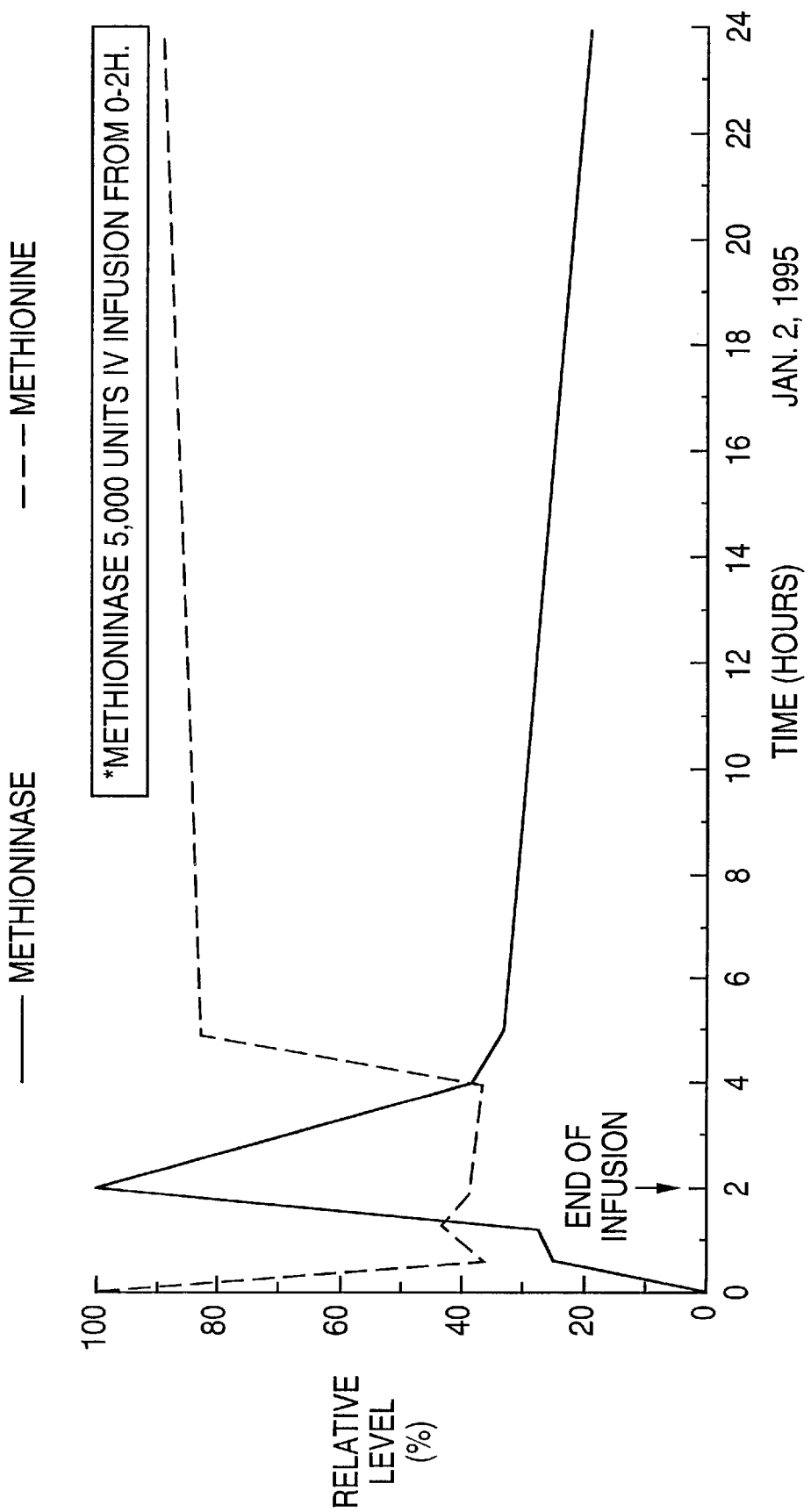
FIG. 15 provides a pharmacokinetic evaluation of methioninase in a human patient.
Figure 16:
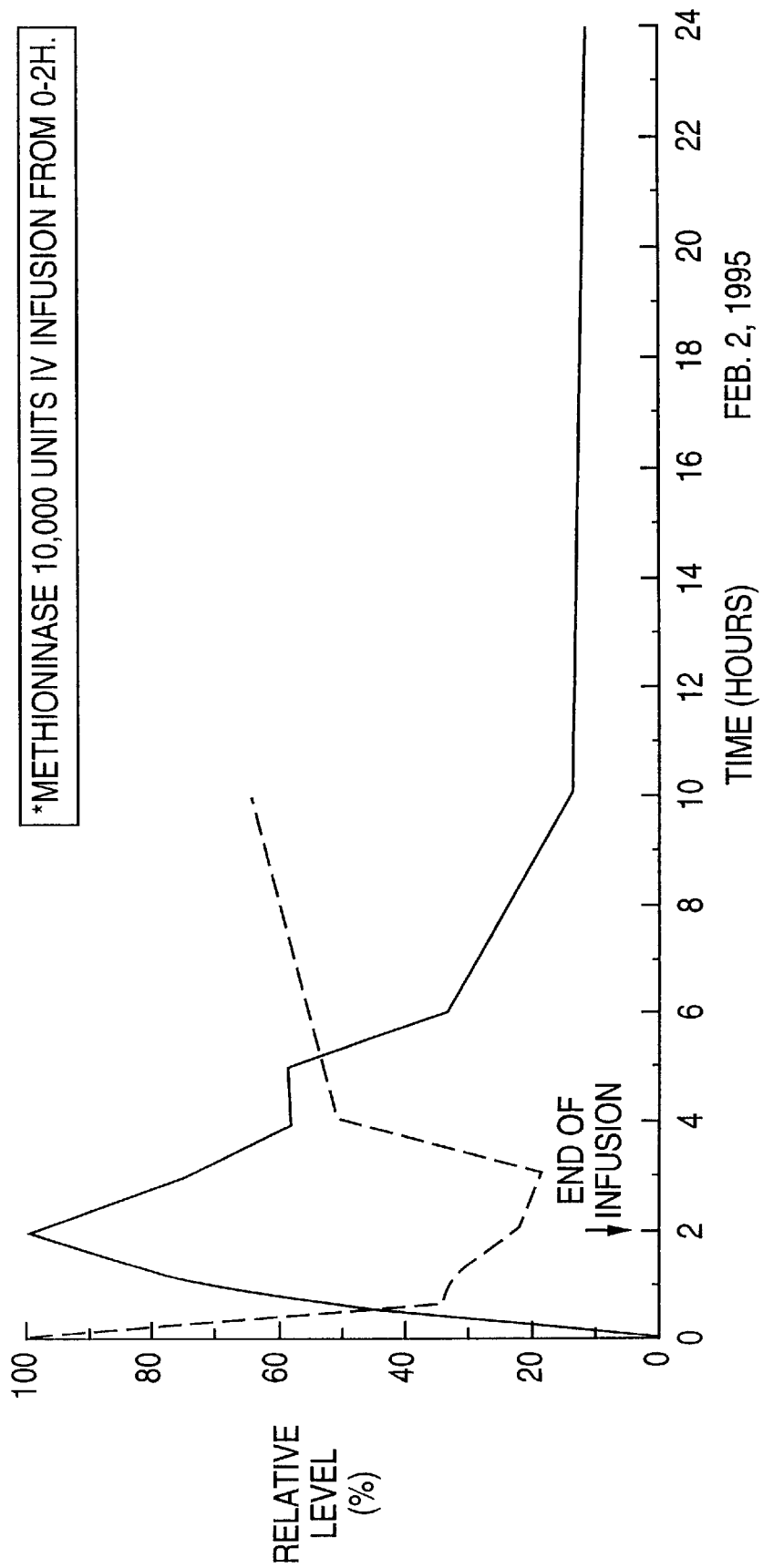
FIG. 16 provides a pharmacokinetic evaluation of methioninase in a human patient.
Figure 17:
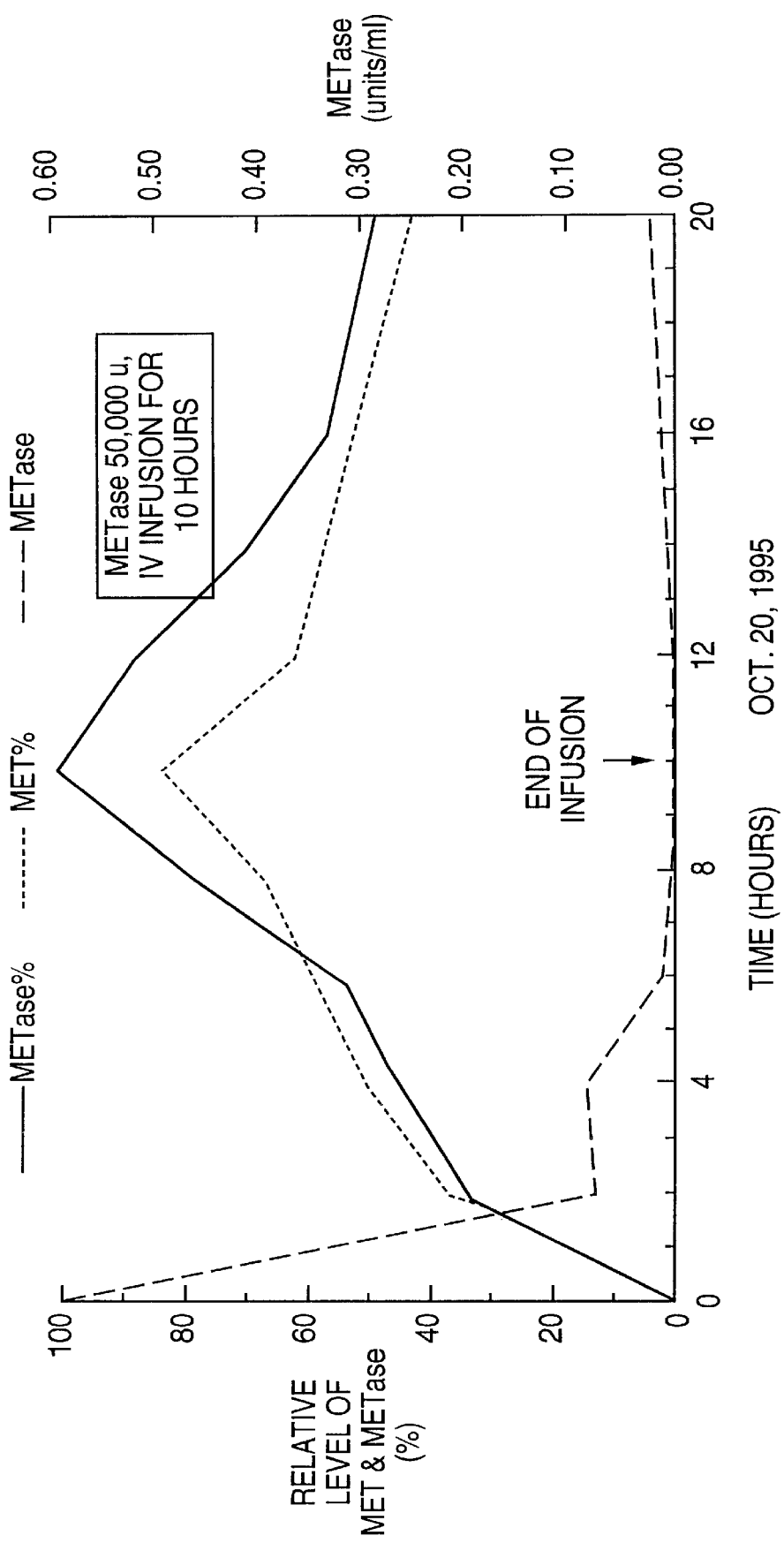
FIG. 17 provides a pharmacokinetic evaluation of methioninase in a human patient.

KB3–1 cells (Human squamous cell carcinoma) were grown in RPMI 1640 medium supplemented with 10% FBS. Various concentrations of rMETase were added to the medium and incubated at 37° C., 5% $CO_2$. The relative cell number was measured at $OD_{570}$. The results demonstrated that rMETase effectively inhibited cell growth (FIG. 9)

2. Growth Inhibition of KB3-1 Cells by rMETase in Nude Mice $2 \times 10^5$ cells were injected into Balb/c nu/nu, female, mice in groups of eight. Control: normal saline. Group I: rMETase 30 units, Group II: rMETase 100 units; ip twice a day from day 5 to day 14. The tumor size and body weight were measured. The blood was collected on day 18. The results demonstrated that rMETase effectively inhibited tumor growth without loss of body weight and effected on blood cell production (FIGS. 10–14).

3. Pilot Phase I Clinical Trial of Purified, Natural METase

A pilot Phase I clinical trial has been initiated in order to determine methioninase toxicity, pharmacokinetics of methioninase and methionine-depletion and maximum tolerated dose. A two hour i.v. infusion of 5,000 units (0.4 g) and 10,000 units (0.8 g) and a ten hour i.v. infusion of 20,000 units (1.6 g) of methioninase has been administered into patient-1, patient-2, arid patient-3, respectively. All patients had advanced breast cancer. Blood and urine samples were obtained at frequent intervals from 0 to 24 hours. The toxicity evaluations were carried out according to WHO criteria. Pharmacokinetics data were obtained for both methioninase and methionine levels in the serum, FIGS. 15–18. No acute clinical toxicity was observed whatsoever with all toxicity criteria measured in patient-1, patient-2 and patient-3. The depletion of serum methionine started within 30 min. of the infusion, and was maintained for 4 hours after the infusion was completed in patient-1 and patient-2. The lowest serum methionine levels were 35% and 19% of the pretreatment level, respectively, in patient-1 and patient-2. Patient-3 who received a ten hour i.v. infusion of 20,000 units of recombinant methioninase without any signs of side effects maintained serum levels of recombinant methioninase as high as 50% of the maximum level for a subsequent 10 hours after infusion. Methionine was depleted over 200-fold from 23.1 $\mu$M to 0.1 $\mu$M to 10 hours of infusion. No clinical toxicity was observed whatsoever in all the toxicity criteria measured in patient-3. The results of recombinant methioninase pilot Phase I clinical trial suggested that i.v. infusion of recombinant methioninase is safe and effectively depletes serum methionine without any signs of side effects. Clinical studies are continuing to determine the maximum length of time essentially complete serum methionine depletion can be tolerated in order to proceed to efficacy studies.

4. Pilot Phase I Clinical Trial of Purified, Recombinant METase

Figure 19:
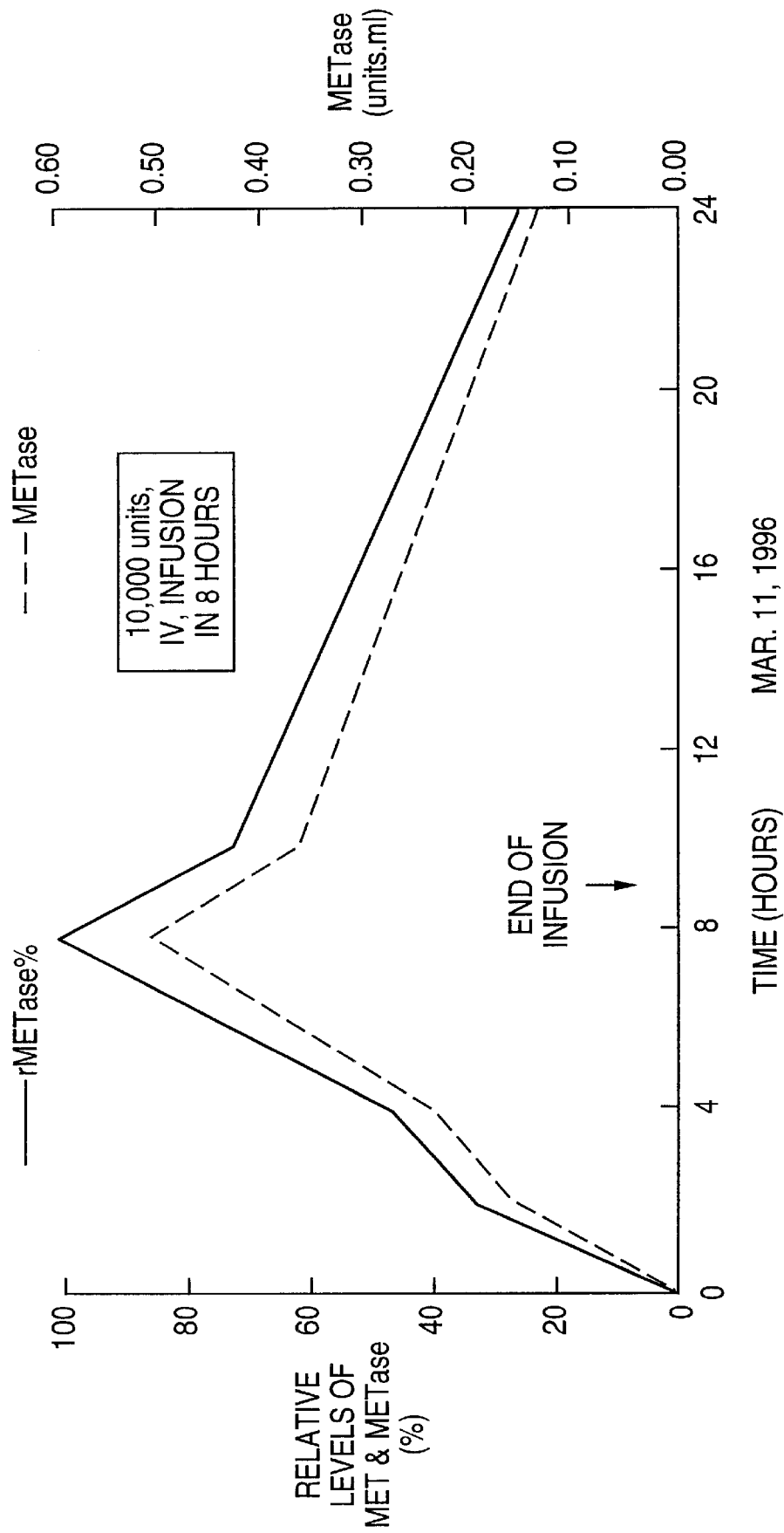
FIG. 19 provides a pharmacokinetic evaluation of rMETase in a human patient.

Patient 1, female, 50 years old, with stage IV breast carcinoma with lymph nodes metastasis, received 20,000 units (0.5 g) rMETase iv infusion for 10 hours. Physical examinations were recorded and blood samples were collected before treatment, during treatment every two hours and two hours and 16 hours after treatment. Laboratory determination were carried according to the WHO criteria. The results showed that the rMETase level was enhanced immediately after the start of the infusion, reached the highest point after 10 hours. Eight hours after the infusion was stopped the level was 50% of the peak and still maintained 20% of the peak 16 hours after the infusion. The results of the laboratory examination were evaluated according to the WHO criteria showed no acute toxicity. FIG. 19.

Patient-2, 48 years old, female, with state IV breast carcinoma with lymph nodes metastasis, received 5,000 units (0.25 g) rMETase by in infusion for 24 hours. Patient-3, 56 years old, female, with stage III renal carcinoma, received 10,000 units (0.5 g) rMETase by iv infusion for 24 hours.

Physical examinations were recorded and the blood samples were collected before treatment, during treatment every two hours and two hours and 48 hours after infusion. Laboratory determinations were carried out according to WHO criteria. The results showed that the rMETase levels were enhanced immediately after the start of the infusion and maintained high level during the infusion. After 48 hours, the methioninase level was dropped back normal.

The serum methionine levels are currently being analyzed.

The results of the laboratory examinations were evaluated according to WHO criteria and showed no acute toxicity (Tables 2 and 3). The result suggested that rMETase did not cause any toxicity in patient-2 and patient-3.

TABLE 2

PROTOCOL OF rMETase CLINICAL PHASE I TRIAL

| | Patient I | Patient II | Patient III |
| --- | --- | --- | --- |
| Diagnosis | Breast cancer with metastasis | | Renal cancer |
| Sex | Female | Female | Female |
| Age | 50 | 48 | 56 |
| Methioninase | 10,000 units | 5000 units | 10,000 units |
| i.v. infusion | 8 hours | 24 hours | 24 hours |
| Blood collection | Before infusion and during infusion every two hours, After infusion 48 hours | | |
| Evaluation | WHO Criteria | | |

AntiCancer Inc.

TABLE 3

TOXICITY OF rMETase PILOT-CLINICAL PHASE I TRIAL)

| Physical & Laboratory | Grade | | |
| --- | --- | --- | --- |
| Examination | Patient 1 | Patient 2 | Patient 3 |
| Hematological | 0 | 0 | 0 |
| Gastrointestinal | 0 | 0 | 0 |
| Renal | 0 | 0 | 0 |
| Pulmonary | 0 | 0 | 0 |
| Fever | 0 | 0 | 0 |
| Allergic | 0 | 0 | 0 |
| Phlebitis | 0 | 0 | 0 |
| Cutaneous | 0 | 0 | 0 |
| Cardiac | 0 | 0 | 0 |
| Neurological | 0 | 0 | 0 |

* According to WHO toxicity criteria

I claim:

1. An improved methioninase formulation which formulation is detergent free, has less than one ng endotoxin per mg protein and wherein said methioninase has a specific activity of at least to about 50 U/mg protein, wherein said methioninase is in a form selected from the group consisting of crystalline methioninase, lyophilized methioninase, and methioninase conjugated to a polymer.

2. The formulation of claim 1 wherein said methioninase is crystalline.

3. The formulation of claim 1 wherein said methioninase is lyophilized.

4. The formulation of claim 1 wherein said methioninase is conjugated to a polymer.

5. The formulation of claim 4 wherein said polymer is polyethylene glycol (PEG).

6. The methioninase formulation of claim 5 wherein the PEG has a molecular weight of at least about 5,000.

7. The formulation of claim 1, wherein said methioninase has the amino acid sequence as depicted in SEQ ID NO:2.

8. A method for making the lyophilized methioninase formulation of claim 3, comprising the step of lyophilizing a frozen buffered, salt solution comprising from about 10 mg/ml to about 20 mg/ml of methioninase in a vacuum.

9. The formulation of claim 7, wherein said methioninase is conjugated to a polymer.

10. A method for making the crystallized methioninase formulation of claim 2, comprising the step of subjecting a frozen salt-free solution of methioninase to a vacuum.

11. The methioninase formulation of claim 1 wherein said methioninase is extended with histidine residues.

12. The formulation of claim 2 wherein said methioninase is extended with histidine residues.

13. The formulation of claim 3 wherein said methioninase is extended with histidine residues.

14. The formulation of claim 4 wherein said methioninase is extended with histidine residues.

15. The method of claim 8 wherein said methioninase is extended with histidine residues.

16. The formulation of claim 9 wherein said methioninase is extended with histidine residues.

17. The formulation of claim 9 wherein said polymer is polyethylene glycol.

18. The formulation of claim 7 wherein said methioninase is lyophilized.

19. The formulation of claim 7 wherein said methioninase is crystalline.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1369 base pairs
        ( B ) TYPE: nucleic acid
        ( C ) STRANDEDNESS: double
        ( D ) TOPOLOGY: linear ( i i ) MOLECULE TYPE: Genomic DNA ( i v ) ANTI-SENSE: NO ( i x ) FEATURE:
        ( A ) NAME/KEY: Coding Sequence
        ( B ) LOCATION: 48...1241
        ( D ) OTHER INFORMATION:

( x i ) SEQUENCE DESCRIPTION: SEQ ID NO:1:

```
GCCGGTCTGT  GGAATAAGCT  TATAACAAAC  CACAAGAGGC  GGTTGCC  ATG  CAC  GGC                  56
                                                         Met  His  Gly
                                                          1

TCC  AAC  AAG  CTC  CCA  GGA  TTT  GCC  ACC  CGC  GCC  ATT  CAC  CAT  GGC  TAC         104
Ser  Asn  Lys  Leu  Pro  Gly  Phe  Ala  Thr  Arg  Ala  Ile  His  His  Gly  Tyr
      5                   10                        15

GAC  CCC  CAG  GAC  CAC  GGC  GGC  GCA  CTG  GTG  CCA  CCG  GTC  TAC  CAG  ACC         152
Asp  Pro  Gln  Asp  His  Gly  Gly  Ala  Leu  Val  Pro  Pro  Val  Tyr  Gln  Thr
 20                        25                        30                        35

GCG  ACG  TTC  ACC  TTC  CCC  ACC  GTG  GAA  TAC  GGC  GCT  GCG  TGC  TTT  GCC         200
Ala  Thr  Phe  Thr  Phe  Pro  Thr  Val  Glu  Tyr  Gly  Ala  Ala  Cys  Phe  Ala
                     40                        45                        50

GGC  GAG  CAG  GCC  GGC  CAT  TTC  TAC  AGC  CGC  ATC  TCC  AAC  CCC  ACC  CTC         248
Gly  Glu  Gln  Ala  Gly  His  Phe  Tyr  Ser  Arg  Ile  Ser  Asn  Pro  Thr  Leu
           55                        60                        65

AAC  CTG  CTG  GAA  GCA  CGC  ATG  GCC  TCG  CTG  GAA  GGC  GGC  GAG  GCC  GGG         296
Asn  Leu  Leu  Glu  Ala  Arg  Met  Ala  Ser  Leu  Glu  Gly  Gly  Glu  Ala  Gly
      70                        75                        80

CTG  GCG  CTG  GCC  TCG  GGC  ATG  GGG  GCG  ATC  ACG  TCC  ACG  CTA  TGG  ACA         344
Leu  Ala  Leu  Ala  Ser  Gly  Met  Gly  Ala  Ile  Thr  Ser  Thr  Leu  Trp  Thr
 85                        90                        95

CTG  CTG  CGC  CCC  GGT  GAC  GAG  GTG  CTG  CTG  GGC  AAC  ACC  CTG  TAC  GGC         392
Leu  Leu  Arg  Pro  Gly  Asp  Glu  Val  Leu  Leu  Gly  Asn  Thr  Leu  Tyr  Gly
100                       105                       110                       115

TGC  ACC  TTT  GCC  TTC  CTG  CAC  CAC  GGC  ATC  GGC  GAG  TTC  GGG  GTC  AAG         440
Cys  Thr  Phe  Ala  Phe  Leu  His  His  Gly  Ile  Gly  Glu  Phe  Gly  Val  Lys
                     120                       125                       130

CTG  CGC  CAT  GTG  GAC  ATG  GCC  GAC  CTG  CAG  GCA  CTG  GAG  GCG  GCC  ATG         488
Leu  Arg  His  Val  Asp  Met  Ala  Asp  Leu  Gln  Ala  Leu  Glu  Ala  Ala  Met
           135                       140                       145

ACG  CCG  GCC  ACC  CGG  GTG  ATC  TAT  TTC  GAG  TCG  CCG  GCC  AAC  CCC  AAC         536
Thr  Pro  Ala  Thr  Arg  Val  Ile  Tyr  Phe  Glu  Ser  Pro  Ala  Asn  Pro  Asn
                150                       155                       160

ATG  CAC  ATG  GCC  GAT  ATC  GCC  GGC  GTG  GCG  AAG  ATT  GCA  CGC  AAG  CAC         584
Met  His  Met  Ala  Asp  Ile  Ala  Gly  Val  Ala  Lys  Ile  Ala  Arg  Lys  His
      165                       170                       175

GGC  GCG  ACC  GTG  GTG  GTC  GAC  AAC  ACC  TAC  TGC  ACG  CCG  TAC  CTG  CAA         632
Gly  Ala  Thr  Val  Val  Val  Asp  Asn  Thr  Tyr  Cys  Thr  Pro  Tyr  Leu  Gln
180                       185                       190                       195

CGG  CCA  CTG  GAG  CTG  GGC  GCC  GAC  CTG  GTG  GTG  CAT  TCG  GCC  ACC  AAG         680
```

```
Arg  Pro  Leu  Glu  Leu  Gly  Ala  Asp  Leu  Val  Val  His  Ser  Ala  Thr  Lys
               200                      205                      210

TAC  CTG  AGC  GGC  CAT  GGC  GAC  ATC  ACT  GCT  GGC  ATT  GTG  GTG  GGC  AGC    728
Tyr  Leu  Ser  Gly  His  Gly  Asp  Ile  Thr  Ala  Gly  Ile  Val  Val  Gly  Ser
               215                      220                      225

CAG  GCA  CTG  GTG  GAC  CGT  ATA  CGT  CTG  CAG  GGC  CTC  AAG  GAC  ATG  ACC    776
Gln  Ala  Leu  Val  Asp  Arg  Ile  Arg  Leu  Gln  Gly  Leu  Lys  Asp  Met  Thr
               230                      235                      240

GGT  GCG  GTG  CTC  TCG  CCC  CAT  GAC  GCC  GCA  CTG  TTG  ATG  CGC  GGC  ATC    824
Gly  Ala  Val  Leu  Ser  Pro  His  Asp  Ala  Ala  Leu  Leu  Met  Arg  Gly  Ile
     245                      250                      255

AAG  ACC  CTC  AAC  CTG  CGC  ATG  GAC  CGC  CAC  TGC  GCC  AAC  GCT  CAG  GTG    872
Lys  Thr  Leu  Asn  Leu  Arg  Met  Asp  Arg  His  Cys  Ala  Asn  Ala  Gln  Val
260                      265                      270                      275

CTG  GCC  GAG  TTC  CTC  GCC  CGG  CAG  CCG  CAG  GTG  GAG  CTG  ATC  CAT  TAC    920
Leu  Ala  Glu  Phe  Leu  Ala  Arg  Gln  Pro  Gln  Val  Glu  Leu  Ile  His  Tyr
               280                      285                      290

CCG  GGC  CTG  GCG  AGC  TTC  CCG  CAG  TAC  ACC  CTG  GCC  CGC  CAG  CAG  ATG    968
Pro  Gly  Leu  Ala  Ser  Phe  Pro  Gln  Tyr  Thr  Leu  Ala  Arg  Gln  Gln  Met
               295                      300                      305

AGC  CAG  CCG  GGC  GGC  ATG  ATC  GCC  TTC  GAA  CTC  AAG  GGC  GGC  ATC  GGT   1016
Ser  Gln  Pro  Gly  Gly  Met  Ile  Ala  Phe  Glu  Leu  Lys  Gly  Gly  Ile  Gly
               310                      315                      320

GCC  GGG  CGG  CGG  TTC  ATG  AAC  GCC  CTG  CAA  CTG  TTC  AGC  CGC  GCG  GTG   1064
Ala  Gly  Arg  Arg  Phe  Met  Asn  Ala  Leu  Gln  Leu  Phe  Ser  Arg  Ala  Val
     325                      330                      335

AGC  CTG  GGC  GAT  GCC  GAG  TCG  CTG  GCG  CAG  CAC  CCG  GCA  AGC  ATG  ACT   1112
Ser  Leu  Gly  Asp  Ala  Glu  Ser  Leu  Ala  Gln  His  Pro  Ala  Ser  Met  Thr
340                      345                      350                      355

CAT  TCC  AGC  TAT  ACC  CCA  GAG  GAG  CGT  GCG  CAT  TAC  GGC  ATC  TCC  GAG   1160
His  Ser  Ser  Tyr  Thr  Pro  Glu  Glu  Arg  Ala  His  Tyr  Gly  Ile  Ser  Glu
               360                      365                      370

GGG  CTG  GTG  CGG  TTG  TCG  GTG  GGG  CTG  GAA  GAC  ATC  GAC  GAC  CTG  CTG   1208
Gly  Leu  Val  Arg  Leu  Ser  Val  Gly  Leu  Glu  Asp  Ile  Asp  Asp  Leu  Leu
               375                      380                      385

GCC  GAT  GTG  CAA  CAG  GCA  CTC  AAG  GCG  AGT  GCC  TGAACCCGTC ACGGATGAGG    1261
Ala  Asp  Val  Gln  Gln  Ala  Leu  Lys  Ala  Ser  Ala
               390                      395

TCAATGCAAT GGTGGCAATG ATGAACTTG TGCCTGGCGA CGGCGTGCCC GGTGACAGCG              1321

ACCCTGGCGA AACTGCAGAG TGGCTGGAGG CGCTGGAGTC GACCCTGG                          1369
```

( 2 ) INFORMATION FOR SEQ ID NO:2:

( i ) SEQUENCE CHARACTERISTICS:
        ( A ) LENGTH: 398 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Met  His  Gly  Ser  Asn  Lys  Leu  Pro  Gly  Phe  Ala  Thr  Arg  Ala  Ile  His
 1                  5                   10                      15

His  Gly  Tyr  Asp  Pro  Gln  Asp  His  Gly  Gly  Ala  Leu  Val  Pro  Pro  Val
               20                      25                      30

Tyr  Gln  Thr  Ala  Thr  Phe  Thr  Phe  Pro  Thr  Val  Glu  Tyr  Gly  Ala  Ala
               35                      40                      45

Cys  Phe  Ala  Gly  Glu  Gln  Ala  Gly  His  Phe  Tyr  Ser  Arg  Ile  Ser  Asn
```

|  |  |  |  | 50 |  |  |  |  | 55 |  |  |  |  | 60 |  |
|---|---|---|---|---|---|---|---|---|---|---|---|---|---|---|---|
| Pro<br>65 | Thr | Leu | Asn | Leu | Leu<br>70 | Glu | Ala | Arg | Met | Ala<br>75 | Ser | Leu | Glu | Gly | Gly<br>80 |
| Glu | Ala | Gly | Leu | Ala<br>85 | Leu | Ala | Ser | Gly | Met<br>90 | Gly | Ala | Ile | Thr | Ser<br>95 | Thr |
| Leu | Trp | Thr | Leu<br>100 | Leu | Arg | Pro | Gly | Asp<br>105 | Glu | Val | Leu | Leu | Gly<br>110 | Asn | Thr |
| Leu | Tyr | Gly<br>115 | Cys | Thr | Phe | Ala | Phe<br>120 | Leu | His | His | Gly | Ile<br>125 | Gly | Glu | Phe |
| Gly | Val<br>130 | Lys | Leu | Arg | His | Val<br>135 | Asp | Met | Ala | Asp | Leu<br>140 | Gln | Ala | Leu | Glu |
| Ala<br>145 | Ala | Met | Thr | Pro | Ala<br>150 | Thr | Arg | Val | Ile | Tyr<br>155 | Phe | Glu | Ser | Pro | Ala<br>160 |
| Asn | Pro | Asn | Met | His<br>165 | Met | Ala | Asp | Ile | Ala<br>170 | Gly | Val | Ala | Lys | Ile<br>175 | Ala |
| Arg | Lys | His | Gly<br>180 | Ala | Thr | Val | Val<br>185 | Asp | Asn | Thr | Tyr | Cys<br>190 | Thr | Pro |  |
| Tyr | Leu | Gln<br>195 | Arg | Pro | Leu | Glu | Leu<br>200 | Gly | Ala | Asp | Leu | Val<br>205 | Val | His | Ser |
| Ala | Thr<br>210 | Lys | Tyr | Leu | Ser | Gly<br>215 | His | Gly | Asp | Ile | Thr<br>220 | Ala | Gly | Ile | Val |
| Val<br>225 | Gly | Ser | Gln | Ala | Leu<br>230 | Val | Asp | Arg | Ile | Arg<br>235 | Leu | Gln | Gly | Leu | Lys<br>240 |
| Asp | Met | Thr | Gly | Ala<br>245 | Val | Leu | Ser | Pro | His<br>250 | Asp | Ala | Ala | Leu | Leu<br>255 | Met |
| Arg | Gly | Ile | Lys<br>260 | Thr | Leu | Asn | Leu | Arg<br>265 | Met | Asp | Arg | His | Cys<br>270 | Ala | Asn |
| Ala | Gln | Val<br>275 | Leu | Ala | Glu | Phe | Leu<br>280 | Ala | Arg | Gln | Pro | Gln<br>285 | Val | Glu | Leu |
| Ile | His<br>290 | Tyr | Pro | Gly | Leu | Ala<br>295 | Ser | Phe | Pro | Gln | Tyr<br>300 | Thr | Leu | Ala | Arg |
| Gln<br>305 | Gln | Met | Ser | Gln | Pro<br>310 | Gly | Gly | Met | Ile | Ala<br>315 | Phe | Glu | Leu | Lys | Gly<br>320 |
| Gly | Ile | Gly | Ala | Gly<br>325 | Arg | Arg | Phe | Met | Asn<br>330 | Ala | Leu | Gln | Leu | Phe<br>335 | Ser |
| Arg | Ala | Val | Ser<br>340 | Leu | Gly | Asp | Ala | Glu<br>345 | Ser | Leu | Ala | Gln | His<br>350 | Pro | Ala |
| Ser | Met | Thr<br>355 | His | Ser | Ser | Tyr | Thr<br>360 | Pro | Glu | Glu | Arg | Ala<br>365 | His | Tyr | Gly |
| Ile | Ser<br>370 | Glu | Gly | Leu | Val | Arg<br>375 | Leu | Ser | Val | Gly | Leu<br>380 | Glu | Asp | Ile | Asp |
| Asp<br>385 | Leu | Leu | Ala | Asp | Val<br>390 | Gln | Gln | Ala | Leu | Lys<br>395 | Ala | Ser | Ala |  |  |

(2) INFORMATION FOR SEQ ID NO:3:

(i) SEQUENCE CHARACTERISTICS:
        (A) LENGTH: 1369 base pairs
        (B) TYPE: nucleic acid
        (C) STRANDEDNESS: single
        (D) TOPOLOGY: linear (i i) MOLECULE TYPE: Genomic DNA (i v) ANTI-SENSE: YES (x i) SEQUENCE DESCRIPTION: SEQ ID NO:3:

| | | | | | |
|---|---|---|---|---|---|
| CCAGGGTCGA | CTCCAGCGCC | TCCAGCCACT | CTGCAGTTTC | GCCAGGGTCG | CTGTCACCGG | 60
| GCACGCCGTC | GCCAGGCACA | AGGTTCATCA | TTGCCACCAT | TGCATTGACC | TCATCCGTGA | 120
| CGGGTTCAGG | CACTCGCCTT | GAGTGCCTGT | TGCACATCGG | CCAGCAGGTC | GTCGATGTCT | 180
| TCCAGCCCCA | CCGACAACCG | CACCAGCCCC | TCGGAGATGC | CGTAATGCGC | ACGCTCCTCT | 240
| GGGGTATAGC | TGGAATGAGT | CATGCTTGCC | GGGTGCTGCG | CCAGCGACTC | GGCATCGCCC | 300
| AGGCTCACCG | CGCGGCTGAA | CAGTTGCAGG | GCGTTCATGA | ACCGCCGCCC | GGCACCGATG | 360
| CCGCCCTTGA | GTTCGAAGGC | GATCATGCCG | CCCGGCTGGC | TCATCTGCTG | GCGGGCCAGG | 420
| GTGTACTGCG | GGAAGCTCGC | CAGGCCCGGG | TAATGGATCA | GCTCCACCTG | CGGCTGCCGG | 480
| GCGAGGAACT | CGGCCAGCAC | CTGAGCGTTG | GCGCAGTGGC | GGTCCATGCG | CAGGTTGAGG | 540
| GTCTTGATGC | CGCGCATCAA | CAGTGCGGCG | TCATGGGGCG | AGAGCACCGC | ACCGGTCATG | 600
| TCCTTGAGGC | CCTGCAGACG | TATACGGTCC | ACCAGTGCCT | GGCTGCCCAC | CACAATGCCA | 660
| GCAGTGATGT | CGCCATGGCC | GCTCAGGTAC | TTGGTGGCCG | AATGCACCAC | CAGGTCGGCG | 720
| CCCAGCTCCA | GTGGCCGTTG | CAGGTACGGC | GTGCAGTAGG | TGTTGTCGAC | CACCACGGTC | 780
| GCGCCGTGCT | TGCGTGCAAT | CTTCGCCACG | CCGGCGATAT | CGGCCATGTG | CATGTTGGGG | 840
| TTGGCCGGCG | ACTCGAAATA | GATCACCCGG | GTGGCCGGCG | TCATGGCCGC | CTCCAGTGCC | 900
| TGCAGGTCGG | CCATGTCCAC | ATGGCGCAGC | TTGACCCCGA | ACTCGCCGAT | GCCGTGGTGC | 960
| AGGAAGGCAA | AGGTGCAGCC | GTACAGGGTG | TTGCCCAGCA | GCACCTCGTC | ACCGGGGCGC | 1020
| AGCAGTGTCC | ATAGCGTGGA | CGTGATCGCC | CCCATGCCCG | AGGCCAGCGC | CAGCCCGGCC | 1080
| TCGCCGCCTT | CCAGCGAGGC | CATGCGTGCT | TCCAGCAGGT | TGAGGGTGGG | GTTGGAGATG | 1140
| CGGCTGTAGA | AATGGCCGGC | CTGCTCGCCG | GCAAAGCACG | CAGCGCCGTA | TTCCACGGTG | 1200
| GGGAAGGTGA | ACGTCGCGGT | CTGGTAGACC | GGTGGCACCA | GTGCGCCGCC | GTGGTCCTGG | 1260
| GGGTCGTAGC | CATGGTGAAT | GGCGCGGGTG | GCAAATCCTG | GGAGCTTGTT | GGAGCCGTGC | 1320
| ATGGCAACCG | CCTCTTGTGG | TTTGTTATAA | GCTTATTCCA | CAGACCGGC | | 1369

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: NO ( x i ) SEQUENCE DESCRIPTION: SEQ ID NO:4:

GCCGGTCTGT    GGAATAAGCT                                  20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:5:

CCAGGGTCGA    CTCCAGCGCC                                  20

( 2 ) INFORMATION FOR SEQ ID NO:6:

( i ) SEQUENCE CHARACTERISTICS:

-continued (A) LENGTH: 29 base pairs
(B) TYPE: nucleic acid
(C) STRANDEDNESS: single
(D) TOPOLOGY: linear (iv) ANTI-SENSE: NO (xi) SEQUENCE DESCRIPTION: SEQ ID NO:6:

GGAATTCCAT ATGCACGGCT CCAACAAGC        29

(2) INFORMATION FOR SEQ ID NO:7:

(i) SEQUENCE CHARACTERISTICS:
(A) LENGTH: 51 base pairs
(B) TYPE: nucleic acid
(C) STRANDEDNESS: single
(D) TOPOLOGY: linear (iv) ANTI-SENSE: YES (xi) SEQUENCE DESCRIPTION: SEQ ID NO:7:

AGTCATCCTA GGTCACATCA TCATCATCAT CATGGCACTC GCCTTGAGTG C        51

(2) INFORMATION FOR SEQ ID NO:8:

(i) SEQUENCE CHARACTERISTICS:
(A) LENGTH: 33 base pairs
(B) TYPE: nucleic acid
(C) STRANDEDNESS: single
(D) TOPOLOGY: linear (iv) ANTI-SENSE: YES (xi) SEQUENCE DESCRIPTION: SEQ ID NO:8:

AGTCATCCTA GGTCAGGCAC TCGCCTTGAG TGC        33